United States Patent
Shimizu et al.

(10) Patent No.: US 10,071,045 B2
(45) Date of Patent: *Sep. 11, 2018

(54) COSMETIC COMPOSITION COMPRISING A HYDROCARBONATED-BASED RESIN, A HYDROCARBON-BASED BLOCK COPOLYMER, A NON VOLATILE DIMETHICONE OIL AND A NON VOLATILE HYDROCARBONATED OIL

(71) Applicant: L'OREAL, Paris (FR)

(72) Inventors: Momoko Shimizu, Kawasaki (JP); Annabelle Servais-Dealet, Bry sur Marne (FR); Maki Ishida, Asaka (JP)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/408,727

(22) PCT Filed: Jun. 21, 2013

(86) PCT No.: PCT/JP2013/067745
§ 371 (c)(1),
(2) Date: Dec. 17, 2014

(87) PCT Pub. No.: WO2013/191303
PCT Pub. Date: Dec. 27, 2013

(65) Prior Publication Data
US 2015/0182440 A1 Jul. 2, 2015

(30) Foreign Application Priority Data
Jun. 21, 2012 (WO) .................. PCT/JP2012/066470

(51) Int. Cl.
| | | |
|---|---|---|
| *A61K 8/81* | (2006.01) | |
| *A61K 8/891* | (2006.01) | |
| *A61Q 1/04* | (2006.01) | |
| *A61K 8/31* | (2006.01) | |
| *A61Q 1/06* | (2006.01) | |
| *A61K 8/90* | (2006.01) | |
| *A61K 8/02* | (2006.01) | |
| *A61Q 1/02* | (2006.01) | |
| *A61Q 1/08* | (2006.01) | |

(52) U.S. Cl.
CPC .......... *A61K 8/8111* (2013.01); *A61K 8/0279* (2013.01); *A61K 8/31* (2013.01); *A61K 8/8117* (2013.01); *A61K 8/891* (2013.01); *A61K 8/90* (2013.01); *A61Q 1/04* (2013.01); *A61Q 1/06* (2013.01); *A61K 2800/59* (2013.01); *A61Q 1/02* (2013.01); *A61Q 1/08* (2013.01)

(58) Field of Classification Search
CPC ........ A61K 8/31; A61K 8/891; A61K 8/0279; A61K 8/8111; A61K 8/8117; A61Q 1/04
See application file for complete search history.

(56) References Cited

U.S. PATENT DOCUMENTS

| | | |
|---|---|---|
| 5,156,911 A | 10/1992 | Stewart |
| 5,221,534 A | 6/1993 | DesLauriers et al. |
| 5,519,063 A | 5/1996 | Mondet et al. |
| 5,736,125 A | 4/1998 | Morawsky et al. |
| 5,750,723 A | 5/1998 | Eldin et al. |
| 5,847,156 A | 12/1998 | Eldin et al. |
| 6,048,918 A | 4/2000 | Eldin et al. |
| 6,180,123 B1 | 1/2001 | Mondet et al. |
| 6,491,927 B1 | 12/2002 | Arnaud et al. |
| 6,682,748 B1 | 1/2004 | De La Poterie et al. |
| 7,470,725 B2 | 12/2008 | Schwertfeger et al. |
| 7,993,661 B2 | 8/2011 | Arnaud et al. |
| 8,246,939 B2 * | 8/2012 | Bobka ............ A61K 8/02 424/400 |
| 8,252,270 B2 | 8/2012 | Jacques et al. |
| 8,357,354 B2 | 1/2013 | Ilekti et al. |
| 8,658,141 B2 | 2/2014 | Bui et al. |
| 2002/0055562 A1 | 5/2002 | Butuc |
| 2002/0058054 A1 | 5/2002 | Arnaud |
| 2002/0187116 A1 | 12/2002 | De La Poterie |
| 2004/0234612 A1 | 11/2004 | Blin et al. |
| 2005/0008592 A1 | 1/2005 | Gardel et al. |
| 2006/0193808 A1 | 8/2006 | Auguste |

(Continued)

FOREIGN PATENT DOCUMENTS

| | | |
|---|---|---|
| CN | 1346629 A | 5/2002 |
| EP | 0542669 A1 | 5/1993 |

(Continued)

OTHER PUBLICATIONS

Dow Corning VM-2270 Aerogel Fine Particles (2012).*
Dow Corning, "Xiameter PMX-200 Silicone Fluid", last revised Nov. 14, 2011.*
International Search Report for PCT/JP2013/067746, dated Oct. 18, 2013.
Boutevin, B., et al., "Study of Morphological and Mechanical Properties of PP/PBT," Polymer Bulletin, 34 (1995), pp. 117-123.
Hamley, I.W., "Crystallization in Block Copolymers," Advances in Polymer Science, vol. 148, (1999), pp. 113-137.
Nojima, S., "Melting Behaviour of Poly(δ-caprolactone)-block-polybutadiene Copolymers," Macromolecules, 32, pp. 3727-3734 (1999).

(Continued)

*Primary Examiner* — Gina Chieun Yu Justice
(74) *Attorney, Agent, or Firm* — The Marbury Law Group, PLLC

(57) ABSTRACT

The present invention relates to compositions for making up and/or caring for the skin and/or the lips, comprising at least one fatty phase comprising:—at least one hydrocarbon-based resin with a number-average molecular weight of less than or equal to 10 000 g/mol,—at least one hydrocarbon-based block polymer,—from 11% to 80% by weight of non volatile non phenylated silicone oil(s) having at least a dimethicone part, relative to the total weight of the composition, and—from 1% to 80% by total weight of non volatile hydrocarbonated apolar oil(s), relative to the total weight of the composition.

19 Claims, No Drawings

(56) References Cited

U.S. PATENT DOCUMENTS

| | | |
|---|---|---|
| 2007/0014745 A1 | 1/2007 | Arnaud et al. |
| 2007/0041920 A1 | 2/2007 | Blin et al. |
| 2007/0258923 A1 | 11/2007 | Bui et al. |
| 2007/0258924 A1 | 11/2007 | Bui et al. |
| 2007/0258933 A1 | 11/2007 | Bui et al. |
| 2007/0258934 A1 | 11/2007 | Bui et al. |
| 2008/0085961 A1 | 4/2008 | Lin |
| 2008/0102048 A1 | 5/2008 | McDermott |
| 2008/0102049 A1 | 5/2008 | McDermott |
| 2008/0152678 A1 | 6/2008 | Shah et al. |
| 2008/0171005 A1* | 7/2008 | Jacques ............... A61K 8/8111 424/59 |
| 2008/0171006 A1 | 7/2008 | Bui et al. |
| 2009/0247648 A1 | 10/2009 | Zhao |
| 2011/0002864 A1 | 1/2011 | Ilekti et al. |
| 2011/0020263 A1 | 1/2011 | Ilekti et al. |
| 2011/0142774 A1 | 6/2011 | Tomita et al. |
| 2011/0268675 A1* | 11/2011 | Ureneck ............... A61K 8/25 424/59 |
| 2012/0237467 A1 | 9/2012 | Sasada et al. |
| 2012/0269755 A1 | 10/2012 | Osawa et al. |

FOREIGN PATENT DOCUMENTS

| | | |
|---|---|---|
| EP | 0787730 A1 | 8/1997 |
| EP | 0787731 A2 | 8/1997 |
| EP | 0951897 A2 | 10/1999 |
| EP | 0955039 A1 | 11/1999 |
| EP | 1743626 A1 | 1/2007 |
| EP | 1759690 A2 | 3/2007 |
| EP | 1935400 A1 | 6/2008 |
| EP | 1944015 A2 | 7/2008 |
| EP | 2263640 A1 | 12/2010 |
| FR | 2931673 A1 | 12/2009 |
| JP | 11236314 A | 8/1999 |
| JP | 2007-297391 A | 11/2007 |
| JP | 2007297392 A | 11/2007 |
| JP | 2011-020933 A | 2/2011 |
| JP | 2011140481 A | 7/2011 |
| JP | 2012082188 A | 4/2012 |
| WO | 93/01797 A1 | 2/1993 |
| WO | 96/08537 A1 | 3/1996 |
| WO | 00/49997 A1 | 8/2000 |
| WO | 01/19333 A1 | 3/2001 |
| WO | 2009/150852 A1 | 12/2009 |
| WO | 2011071148 A | 6/2011 |
| WO | 2012/038879 A2 | 3/2012 |
| WO | 2013/191304 A1 | 12/2013 |

OTHER PUBLICATIONS

Rangarajan, P., et al., "Morphology of Semi-Crystalline Block Copolymers of Ethylene-(ethylene-alt-propylene)," 26 (1993), pp. 4640-4645 Macromolecules,.

Richter, P., et al., "Polymer Aggregates with Crystalline Cores: the System (Poly(ethylene)poly(ethylene propylene)," Macromolecules, 30 (1997), pp. 1053-1068.

Satas, Donatas, "Handbook of Pressure Sensitive Adhesive," 3rd Edition, 1989, pp. 609-619.

English language abstract for FR 2931673 (Dec. 4, 2009).

English language abstract for JP 2011-020933 Feb. 3, 2011).

English language abstract is on the front of WO 93/01797 (dated Feb. 4, 1993).

International Search Report and Written Opinion for PCT/JP2013/067745, (dated Oct. 21, 2013).

Chinese Office Action with English translation for counterpart Chinese Application No. 201380031957.6, dated Apr. 27, 2016.

Non-Final Office Action for co-pending U.S. Appl. No. 14/406,872, dated Oct. 23, 2015.

Non-Final Office Action for co-pending U.S. Appl. No. 14/406,872, dated Jun. 30, 2016.

Japanese Office Action for JP 2014-560184, dated Mar. 27 2017, with English Translation.

Japanese Office Action for JP 2014-560576, dated Apr. 3, 2017 with English Translation.

Non Final Office Action for U.S. Appl. No. 14/406,872, dated Jun. 13, 2017.

Final Office Action for U.S. Appl. No. 14/406,872, dated Nov. 3, 2016.

Final Office Action for U.S. Appl. No. 14/406,872, dated Nov. 20, 2017.

Non-Final Office Action for co-pending U.S. Appl. No. 14/046,872, dated Aug. 23, 2015.

Non-Final Office Action for co-pending U.S. Appl. No. 14/046,872, dated Jun. 30, 2016.

Non-Final Office Action for co-pending U.S. Appl. No. 14/406,872, dated Jun. 29, 2018.

* cited by examiner

COSMETIC COMPOSITION COMPRISING A HYDROCARBONATED-BASED RESIN, A HYDROCARBON-BASED BLOCK COPOLYMER, A NON VOLATILE DIMETHICONE OIL AND A NON VOLATILE HYDROCARBONATED OIL

CROSS REFERENCE TO RELATED APPLICATIONS

This is a national stage application of PCT/JP2013/067745, filed internationally on Jun. 21, 2013, which claims priority to Application No. PCT/JP2012/066470, filed on Jun. 21, 2012, both of which are incorporated herein by reference in their entireties.

TECHNICAL FIELD

The present invention relates to a cosmetic composition, more particularly to a cosmetic composition for making up and/or caring for the skin and/or the lips, comprising at least a hydrocarbonated-based resin, a hydrocarbon-based block copolymer, a non volatile dimethicone oil and a non volatile hydrocarbonated apolar oil.

The present invention also relates to the processes using such composition for making up and/or caring for the skin and/or the lips, comprising the application to the skin and/or the lips of such cosmetic composition.

BACKGROUND ART

In general, when women use a makeup product, especially of lips products such as lipstick or lipgloss type, they wish this product to be easy to apply and to have, after application, comfort and good remanence on the skin or the lips, in particular not to be transferred, and in particular no color or a low level of color to be transferred.

Patent application US 2007258933 discloses the use of a hydrocarbon-based resin and of a particular hydrocarbon-based block polymer for obtaining a shiny deposit on the skin or the lips and gloss remanence.

However, the user has a sensation of "tackiness" during the application (difficult to apply) and drying on the skin or the lips of products incorporating these hydrocarbon-based resin and hydrocarbon-based block copolymer. Furthermore, deposits formed from a galenical formulation incorporating such a hydrocarbon-based resin and hydrocarbon-based block copolymers have insufficient color transfer resistance level.

Therefore, it is sought to further improve the cosmetic properties of the said compositions, in particular the applications properties such as the glide and the easiness to apply and to obtain a uniform deposit on the lips and/or the skin, and in particular to have a deposit on the skin and/or the lips that has a good transfer resistance, and in particular a good color transfer resistance. The deposit should also be sparingly tacky or not tacky and have a good shine level.

DISCLOSURE OF INVENTION

The inventors have found, unexpectedly, that it turns out to be possible to overcome this drawback provided that such hydrocarbon-based resin and hydrocarbon-based block copolymer are used in combination with at least 11% of non volatile silicone oil(s) having at least a dimethicone part and a non volatile hydrocarbonated apolar oil(s).

The aim of the present invention is to overcome these drawbacks and to propose a cosmetic composition that is homogenous, stable (for example no separation into two phases, and/or exsudation, and/or sedimentation of the pigments, in particular after 24 hours at room temperature, and preferably after 72 hours at 50° C.), and capable, on the one hand, of affording good cosmetic properties; in particular applications properties such as glide and easiness to apply, in particular on the lips, good adhesion to the support (skin or lips) and thus good remanence of the deposit of the composition, in particular no or low level transfer of the color of the deposit, and forming a non-tacky or sparingly tacky deposit, having a good level of shine.

Thus, according to one of its aspects, the invention relates to a cosmetic composition for making up and/or caring for the skin and/or the lips, comprising in a physiologically acceptable medium, at least one fatty phase comprising:
  at least one hydrocarbon-based resin with a number-average molecular weight of less than or equal to 10 000 g/mol,
  at least one hydrocarbon-based block polymer,
  from 11% to 80% by total weight of non volatile non phenylated silicone oil(s) having at least a dimethicone part, or mixture thereof, relative to the total weight of the composition, and
  from 1% to 80% by weight of non volatile hydrocarbonated apolar oil(s), or mixture thereof, relative to the total weight of the composition.

Such a composition is stable and homogenous, and are preferably makeup compositions, whose deposition on keratin materials, and in particular the lips and/or the skin, is easy to apply (good glide, homogenous deposit) and the deposit has good transfer resistance after application (in particular, no transfer or poor transfer of the color of the deposit, in particular on a cup or a glass while drinking for example). Beside, the deposit obtained with such composition, is sparingly tacky or non-tacky, and has a good level of shine The present invention also relates to a cosmetic process for making up and/or caring for the skin and/or the lips, comprising at least the application to the said skin and/or the said lips of composition comprising, in a physiologically acceptable medium, at least one fatty phase comprising:
  at least one hydrocarbon-based resin with a number-average molecular weight of less than or equal to 10 000 g/mol,
  at least one hydrocarbon-based block polymer,
  from 11% to 80% by total weight of non volatile non phenylated silicone oil(s) having at least a dimethicone part, or mixture thereof, relative to the total weight of the composition, and
  from 1% to 80% by weight of non volatile hydrocarbonated apolar oil(s), relative to the total weight of the composition.

BEST MODE FOR CARRYING OUT THE INVENTION

Advantageously, the composition under consideration according to the invention is an oil-in-oil type composition. In the oil in oil type cosmetic composition of the invention, the non volatile silicone oil and the non volatile hydrocarbon oil is in a stable oil in oil state before application, without being separated from each other. After application, the non volatile silicone oil comes up to the surface of the deposit, and this separated non volatile silicone oil covers an adherent layer of the non volatile hydrocarbonated oil, the hydrocarbon based resin and the hydrocarbon-based block polymer. Therefore, the resulting composition has good transfer resistance and offers a good level of shine. Rubbing the lips again each other during application further enhance this separation.

Advantageously, the composition under consideration according to the invention is anhydrous.

Physiologically Acceptable Medium

For the purposes of the present invention, the term "physiologically acceptable medium" is intended to denote a medium that is suitable for the application of a composition to the skin and/or the lips, for instance the oils or organic solvents commonly used in cosmetic compositions.

The physiologically acceptable medium (acceptable tolerance, toxicology and feel) is generally adapted to the nature of the support onto which the composition is to be applied, and also to the form in which the composition is to be conditioned.

As emerges from the examples below, the combination under consideration according to the invention proves to be most particularly effective for affording a composition whose deposit on the skin or the lips that simultaneously has improved gloss and non transfer properties. Beside, the deposit also exhibit remanence over time, in particular of remanence of the colour of the deposit (no embrittlement or fragmentation of the deposit, which remains homogeneous) and satisfactory comfort properties, both on application (especially glidance, breakdown, thickness and uniformity of the deposit formed, and reduction of the tack on drying) and during wearing, namely softness, absence of a tacky sensation or of a sensation of tautness or dryness.

What is more, in the case of lipsticks (solid or liquid such as gloss), this improvement of non transfer and non tackiness or sparingly tackiness is not obtained at the expense of the shine, which is another property generally sought for a makeup product of this type. Specifically, contrary to all expectation, no matt effect of the cosmetic product containing the combination under consideration according to the invention is noted.

The invention also preferably relates to a composition for making up and/or caring for the skin and/or the lips, comprising, in a physiologically acceptable medium, at least a hydrocarbon-based, at least a hydrocarbon-based block polymer, from 11% to 80% of non volatile non phenylated silicone oil(s) having at least a dimethicone part, or mixture thereof, from 1% to 80% non volatile hydrocarbonated apolar oil(s), or mixture thereof, and at least one colouring agent.

The compositions under consideration according to the invention and used in the processes according to the invention may be in solid or liquid form at 20° C.

According to one preferred embodiment, in particular in the case of a composition intended for caring for and/or making up the lips, the composition used according to the invention is anhydrous or contains less than 3% by weight of water and preferably less than 1% by weight of water, relative to the total weight of the composition.

The term "anhydrous" especially means that water is preferably not deliberately added to the composition, but may be present in trace amount in the various compounds used in the composition.

The composition according to the invention and/or that used according to the process according to the invention may be in the form of a composition for making up the skin and/or the lips, especially for facial or bodily skin; it may be a complexion product such as a foundation, a face powder or an eyeshadow; a lip product such as a lipstick or a lipcare product; a concealer product; a blusher; an eyeliner; a lip pencil or an eye pencil; a body makeup product; a gloss (lip gloss).

According to a first advantageous embodiment of the invention, the composition is intended for making up the lips and it is more particularly a lipstick (lipstick wand) or a gloss (liquid lipstick).

Advantageously, the lipstick compositions according to the invention are anhydrous.

For the purposes of the invention, the term "solid" characterizes the state of the composition at a temperature of 20° C. In particular, a solid composition according to the invention has, at a temperature of 20° C. and at atmospheric pressure (760 mmHg), a hardness of greater than 30 $Nm^{-1}$ and preferably greater than 35 $Nm^{-1}$.

Protocol for Measuring the Hardness:

The hardness of a composition especially of lipstick wand type is measured according to the following protocol:

The stick of lipstick is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 μm in diameter, by moving the wire relative to the stick at a speed of 100 mm/minute.

The hardness of the samples of compositions of the invention, expressed in $Nm^{-1}$, is measured using a DFGS2 tensile testing machine from the company Indelco-Chatillon.

The measurement is repeated three times and then averaged. The average of the three values read using the tensile testing machine mentioned above, noted Y, is given in grams. This average is converted into newtons and then divided by L which represents the longest distance through which the wire passes. In the case of a cylindrical wand, L is equal to the diameter (in meters).

The hardness is converted into $Nm^{-1}$ by the equation below:

$$(Y \times 10^{-3} \times 9.8)/L$$

For a measurement at a different temperature, the stick is stored for 24 hours at this new temperature before the measurement.

According to this measuring method, a solid composition according to the invention has a hardness at 20° C. of greater than or equal to 30 $Nm^{-1}$, preferably greater than 35 $Nm^{-1}$ and preferably greater than 40 $Nm^{-1}$.

Preferably, the composition according to the invention especially has a hardness at 20° C. of less than 500 $Nm^{-1}$, especially less than 400 $Nm^{-1}$ and preferably less than 300 $Nm^{-1}$.

In particular, a composition whose hardness is greater than 30 $Nm^{-1}$ is said to be "solid" at 20° C. and at atmospheric pressure (760 mmHg).

According to a preferred embodiment, the composition according to the invention is liquid at 20° C.

Protocol for Measuring the Viscosity

The viscosity measurement is generally performed at 25° C., using a Rheomat RM180 viscometer equipped with a No. 4 spindle, the measurement being performed after 10 minutes of rotation of the spindle in the composition (after which time stabilization of the viscosity and of the spin speed of the spindle are observed), at a shear rate of 200 rpm.

Preferably, the composition has at 25° C. a viscosity of between 1 and 25 Pa·s, preferably between 2 and 20 Pa·s and preferably between 4 and 17 Pa·s.

Preferably, the viscosity at 25° C. of a composition according to the invention is between 5 and 16 Pa·s.

The terms "between" and "ranging from" should be understood as including the limits.

The example that follows is given as an illustration, without any limiting nature.

The present invention also covers a cosmetic process for making up and/or caring for the lips, comprising at least the application to the said lips of a composition as defined above.

Advantageously, the composition according to the invention comprises less than 5% and better still less than 2% by weight of volatile oil relative to the total weight of the composition. Preferably, the composition according to the invention is free of volatile oil.

Hydrocarbon-Based Resin

The composition according to the invention comprises at least one hydrocarbon-based resin.

Preferably, the resin used in the composition according to the invention (also known as the tackifying resin) has a number-average molecular weight of less than or equal to 10 000 g/mol, especially ranging from 250 to 5000 g/mol, better still less than or equal to 2000 g/mol and especially ranging from 250 to 2000 g/mol.

The number-average molecular weights (Mn) are determined by gel permeation liquid chromatography (THF solvent, calibration curve established with linear polystyrene standards, refractometric detector).

The resin of the composition according to the invention is advantageously a tackifying resin. Such resins are described especially in the Handbook of Pressure Sensitive Adhesive, edited by Donatas Satas, 3rd edition, 1989, pp. 609-619.

Preferably, the hydrocarbon-based resin is chosen from low molecular weight polymers that may be classified, according to the type of monomer they comprise, as:

indene hydrocarbon-based resins, preferably such as resins derived from the polymerization in major proportion of indene monomer and in minor proportion of a monomer chosen from styrene, methylindene and methylstyrene, and mixtures thereof. These resins may optionally be hydrogenated. These resins may have a molecular weight ranging from 290 to 1150 g/mol.

Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp., or the hydrogenated indene/methylstyrene/styrene copolymers sold under the name "Regalite" by the company Eastman Chemical, in particular Regalite R1100, Regalite R1090, Regalite R7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500 g/mol. Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentanediene dimers such as those derived from the polymerization of first monomers chosen from indene and styrene, and of second monomers chosen from cyclopentanediene dimers such as dicyclopentadiene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.; and diene resins of isoprene dimers such as terpenic resins derived from the polymerization of at least one monomer chosen from α-pinene, β-pinene and limonene, and mixtures thereof. These resins can have a molecular weight ranging from 300 to 2000 g/mol. Such resins are sold, for example, under the names Piccolyte A115 and S125 by Hercules or Zonarez 7100 or Zonatac 105 Lite by Arizona Chem.

Mention may also be made of certain modified resins such as hydrogenated resins, for instance those sold under the name Eastotac C6-C20 Polyolefin by the company Eastman Chemical Co., under the reference Escorez 5300 by the company Exxon Chemicals, or the resins Nevillac Hard or Nevroz sold by the company Neville Chem., the resins Piccofyn A-100, Piccotex 100 or Piccovar AP25 sold by the company Hercules or the resin SP-553 sold by the company Schenectady Chemical Co.

According to one preferred embodiment, the hydrocarbon-based resin is chosen from indene hydrocarbon-based resins, aliphatic pentadiene resins, mixed resins of pentanediene and of indene, diene resins of cyclopentanediene dimers and diene resins of isoprene dimers, or mixtures thereof.

Preferably, the composition comprises at least one compound chosen from hydrocarbon-based resins as described previously, especially indene hydrocarbon-based resins and aliphatic pentadiene resins, or mixtures thereof. According to one preferred embodiment, the hydrocarbon-based resin is chosen from indene hydrocarbon-based resins.

According to one preferred embodiment, the resin is chosen from indene/methylstyrene/hydrogenated styrene copolymers.

In particular, use may be made of indene/methylstyrene/hydrogenated styrene copolymers, such as those sold under the name Regalite by the company Eastman Chemical, such as Regalite R 1100, Regalite R 1090, Regalite R-7100, Regalite R 1010 Hydrocarbon Resin and Regalite R 1125 Hydrocarbon Resin.

Preferably, the hydrocarbon-based resin is present in the composition according to the invention in a content ranging from 1% to 45% by weight, preferably ranging from 3% to 30% by weight and more preferentially ranging from 5% to 25% by weight relative to the total weight of the composition.

Preferably, when the composition is in solid form, the hydrocarbon-based resin is present in the composition according to the invention in a content ranging from 3% to 20% by weight and more preferentially ranging from 5% to 15% by weight relative to the total weight of the composition. Preferably, when the composition is in liquid form, the hydrocarbon-based resin is present in the composition according to the invention in a content ranging from 5% to 25% by weight and more preferentially ranging from 8% to 20% by weight relative to the total weight of the composition.

Hydrocarbon-Based Block Copolymer

The composition according to the invention comprises, besides the resin, a hydrocarbon-based block copolymer, preferably a block copolymer that is soluble or dispersible in a liquid fatty phase as defined previously.

The polymeric gelling agent is capable of thickening or gelling the organic phase of the composition. The term "amorphous polymer" means a polymer that does not have a crystalline form. The polymeric gelling agent is also preferably film-forming, i.e. it is capable of forming a film when applied to the skin.

The hydrocarbon-based block copolymer may especially be a diblock, triblock, multiblock, radial or star copolymer, or mixtures thereof.

Such hydrocarbon-based block copolymers are described in patent application US-A-2002/005 562 and in U.S. Pat. No. 5,221,534.

The hydrocarbon-based block copolymer comprises preferably at least a styrene monomer (it is obtained from at least a styrene monomer).

The copolymer may contain at least one block whose glass transition temperature is preferably less than 20° C., preferably less than or equal to 0° C., preferably less than or equal to −20° C. and more preferably less than or equal to −40° C. The glass transition temperature of the said block may be between −150° C. and 20° C. and especially between −100° C. and 0° C.

The hydrocarbon-based block copolymer present in the composition according to the invention is an amorphous copolymer formed by polymerization of an olefin. The olefin may especially be an elastomeric ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the hydrocarbon-based block copolymer is an amorphous block copolymer of styrene and of an olefin.

Block copolymers comprising at least one styrene block and at least one block comprising units chosen from butadiene, ethylene, propylene, butylene and isoprene or a mixture thereof are especially preferred.

According to one preferred embodiment, the hydrocarbon-based block copolymer is hydrogenated to reduce the residual ethylenic unsaturations after the polymerization of the monomers.

In particular, the hydrocarbon-based block copolymer is a copolymer, optionally hydrogenated, containing styrene blocks and ethylene/C3-C4 alkylene blocks.

According to one preferred embodiment, the composition according to the invention comprises at least one diblock copolymer, which is preferably hydrogenated, preferably chosen from styrene-ethylene/propylene copolymers, styrene-ethylene/butadiene copolymers and styrene-ethylene/butylene copolymers. The diblock polymers are especially sold under the name Kraton® G1701E by the company Kraton Polymers.

According to another preferred embodiment, the composition according to the invention comprises at least one triblock copolymer, which is preferably hydrogenated, preferably chosen from styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® G1652, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to one preferred embodiment of the invention, it is especially possible to use a mixture of a styrene-butylene/ethylene-styrene triblock copolymer and of a styrene-ethylene/butylene diblock copolymer, especially the products sold under the name Kraton® G1657M by the company Kraton Polymers.

According to another preferred embodiment, the composition according to the invention comprises a mixture of styrene-butylene/ethylene-styrene hydrogenated triblock copolymer and of ethylene-propylene-styrene hydrogenated star polymer, such a mixture possibly being especially in isododecane or in another oil. Such mixtures are sold, for example, by the company Penreco under the trade names Versagel® M5960 and Versagel® M5670.

Advantageously, a diblock copolymer such as those described previously is used as polymeric gelling agent, in particular a styrene-ethylene/propylene diblock copolymer or a mixture of diblock and triblock copolymers, as described previously.

The hydrocarbon-based block copolymer (or the mixture of hydrocarbon-based block copolymers) may be present in a content ranging from 0.1% to 20% by weight and preferably ranging from 1% to 15% by weight, more preferably from 1 to 10% by weight, relative to the total weight of the composition.

The hydrocarbon-based block copolymer (or the mixture of hydrocarbon-based block copolymers) may be present in a content ranging from 2% to 10% by weight, relative to the total weight of the composition.

Preferably, the weight ratio of the hydrocarbon-based resin to the hydrocarbon-based block copolymer is between 1 and 10.

More preferably, the weight ratio of the hydrocarbon-based resin to the hydrocarbon-based block copolymer is between 1 and 8.

More preferably, the weight ratio of the hydrocarbon-based resin to the hydrocarbon-based block copolymer is between 1 and 5 and preferably between 1 and 3.

Fatty Phase

The composition according to the invention comprises at least one fatty phase and more particularly at least one liquid fatty phase.

Non Volatile Silicone Oil with Dimethicone Part

The composition according to the invention comprises at least one non volatile non phenylated silicone oil having at least a dimethicone part.

More particularly, the composition according to the invention, comprise from 11% to 80% by total weight of non volatile non phenylated silicone oil(s) having at least a dimethicone part, or mixture thereof, relative to the total weight of the composition.

Preferably, the composition according to the invention, comprise from 12% to 60% by weight, preferably from 12% to 40% by total weight of non volatile non phenylated silicone oil(s) having at least a dimethicone part, or mixture thereof, relative to the total weight of the composition.

In particular, a composition according to the invention for caring for and/or making up the lips and more particularly of lipstick or lipgloss type may comprise from 12% to 60% by total weight of non volatile non phenylated silicone oil(s) having at least a dimethicone part, or mixture thereof, relative to the total weight of the composition.

Advantageously, a composition according to the invention for caring for and/or making up the lips and more particularly of lipstick or lipgloss type may comprise from 12% to 40% by total weight of non volatile non phenylated silicone oil(s) having at least a dimethicone part, or mixture thereof, relative to the total weight of the composition.

Advantageously, a composition according to the invention for caring for and/or making up the lips and more particularly of lipstick or lipgloss type may comprise from 12% to 30% by total weight of non volatile non phenylated silicone oil(s) having at least a dimethicone part, or mixture thereof, relative to the total weight of the composition.

The term "oil" means a water-immiscible non-aqueous compound that is liquid at room temperature (25° C.) and at atmospheric pressure (760 mmHg).

The silicone oils that may be used according to the invention are non-volatile.

In particular, the non-volatile silicone oils that may be used in the invention preferably have a viscosity at 25° C. comprised between 9 cSt and 800 000 cSt, preferably less than or equal to 600 000 cSt and preferably less than or equal to 500 000 cSt. The viscosity of these silicone oils may be measured according to standard ASTM D-445.

The term "non-volatile oil" means an oil whose vapour pressure at room temperature and atmospheric pressure is non-zero and less than 0.02 mmHg (2.66 Pa) and better still less than $10^{-3}$ mmHg (0.13 Pa).

The non-volatile silicone oil that may be used in the invention may be chosen especially from silicone oils especially with a viscosity at 25° C. of greater than or equal to 9 centistokes (cSt) ($9 \times 10^{-6}$ m$^2$/s) and preferably less than 800 000 cSt, preferably between 50 and 600 000 cSt and preferably between 100 and 500 000 cSt. The viscosity of this silicone oil may be measured according to standard ASTM D-445.

The expression "Dimethicone" (INCI Name) corresponds to polydimethylsiloxane part (chemical name).

The non volatile silicone oil having at least a dimethicone part can also be called a non volatile "dimethicone oil".

The expression "non phenylated silicone oil" or "non phenyl silicone oil" means a silicon oil having no phenyl substituent.

Preferably these non-volatile non phenylated silicone oils are chosen from:
polydimethylsiloxanes;
alkyl dimethicones;
vinyl methyl methicones;
and also dimethicone modified with optionally fluorinated aliphatic groups, or with functional groups such as hydroxyl, thiol and/or amine groups.

The non volatile non phenylated dimethicone oil is preferably chosen from dimethicone oils, preferably chosen from polydimethylsiloxanes and/or alkyl dimethicones, and mixture thereof.

Preferably, the non-phenylated non-volatile dimethicone oils can be chosen from:
non-volatile polydimethylsiloxanes (PDMS),
PDMSs comprising alkyl or alkoxy groups, which are pendent and/or at the end of the silicone chain, these groups each containing from 2 to 24 carbon atoms, such as cetyl dimethicone sold under the commercial reference ABIL WAX 9801 from Evonik Goldschmidt,
PDMSs comprising aliphatic and/or aromatic groups, or functional groups such as hydroxyl, thiol and/or amine groups,
polyalkylmethylsiloxanes such as cetyl dimethicone sold under the commercial reference ABIL WAX 9801 from Evonik Goldschmidt, or polyalkylmethylsiloxane optionally substituted with a fluorinated group, such as polymethyltrifluoropropyldimethylsiloxanes,
polyalkylmethylsiloxanes substituted with functional groups such as hydroxyl, thiol and/or amine groups,
polysiloxanes modified with fatty acids, fatty alcohols or polyoxyalkylenes,
and mixtures thereof.

The non volatile non phenylated dimethicone oil is preferably chosen from dimethicone oils, preferably chosen from polydimethylsiloxanes.

Such polydimethylsiloxane (having the INCI name dimethicone) may be chosen from the products commercialised under the reference MIRASIL DM 50 from Bluestar, XIAMETER PMX-200 SILICONE FLUID 350CS from Dow Corning, and/or XIAMETER PMX-200 SILICONE FLUID 100CS from Dow Corning, and/or XIAMETER PMX-200 SIL FLUID 1000CS from Dow Corning, and/or XIAMETER PMX-200 SIL FLUID 60,000CS from Dow Corning, and/or XIAMETER PMX-200 SIL FLUID 300,000CS from Dow Corning, and/or XIAMETER PMX-200 SILICONE FLUID 500,000CS from Dow Corning, and PDMS having a viscosity of 10 cSt, and their mixture.

Preferably, the pdms has a viscosity comprised between 10 cSt and 1000 cSt, more preferably between 100 cSt and 500 cSt.

Preferably, the polydimethylsiloxane (having the INCI name dimethicone) are chosen from the products commercialised under the reference MIRASIL DM 50 from Bluestar XIAMETER PMX-200 SILICONE FLUID 350CS from Dow Corning, and/or XIAMETER PMX-200 SILICONE FLUID 100CS from Dow Corning, and their mixture.

Preferably the non volatile non phenylated dimethicone oil is linear.

Preferably, the composition comprises a mixture of non volatile dimethicone oils, preferably, a mixture of at least two different polydimethylsiloxanes.

Preferably, according to this embodiment, the composition comprises a mixture of two non-volatile polydimethylsiloxanes, preferably in a weight ratio comprised between 0.5 and 2.

The non-phenylated linear dimethicone oil may be chosen especially from the silicones of formula (I):

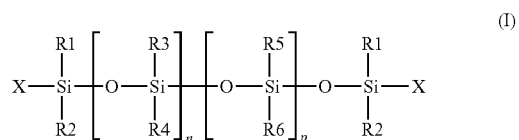

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular whose viscosity at 25° C. is between 9 centistokes (cSt) ($9 \times 10^{-6}$ m$^2$/s) and 800 000 cSt.

As additional non-volatile non phenylated silicone oils that may be used according to the invention, mention may be made of those for which:

- the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
- the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker,
- the substituents $R_1$ to $R_6$ and X represent a methyl group, and p and n are such that the viscosity is 350 cSt, such as the product sold under the name Dow Corning 200 Fluid 350 CS by the company Dow Corning, and
- the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to a particular embodiment, the composition compositions comprises a polyalkylmethylsiloxanes, such as cetyldimethicone sold under the commercial reference ABIL WAX 9801 from Evonik Goldschmidt.

Preferably, the composition comprises from 0.1 to 10% polyalkylmethylsiloxanes, such as cetyldimethicone. It should be noted that, among the abovementioned silicone oils, the phenyl dimethicone silicone oils prove to be particularly advantageous. They can especially impart a good level of gloss to the deposit on the skin or the lips made with the composition according to the invention, without generating any tack, and enable forming a non transfer deposit in association with the non volatile hydrocarbonated apolar oil.

Additional Non Volatile Silicon Oils

The composition according to the invention may comprise at least one additional non volatile silicon oil, different from said non volatile non phenylated silicon oil having at least a dimethicone part.

In particular, said additional silicone oil may be a phenyl silicon oil.

Among these additional silicone oils, two types of oil may be distinguished, according to whether or not they contain a dimethicone part.

Additional Non Volatile Silicone Oil

The composition according to the invention may comprises at least one additional non volatile silicone oil, different from said non volatile non phenylated silicone oil having at least a dimethicone part.

More particularly, the composition according to the invention, may comprise from 0.1% to 50% by total weight of additional non volatile silicone oil(s), or mixture thereof, relative to the total weight of the composition.

In particular, these additional silicone oils may chosen from non volatile phenylated silicone oil.

The expression "phenylated silicone oil" or "phenyl silicone oil" means a silicone oil having at least one phenyl substituent.

Among these additional non volatile phenylated silicone oils, two types of oil may be distinguished, according to whether or not they contain a dimethicone part.

The expression "Dimethicone" (INCI Name) corresponds to polydimethylsiloxane part (chemical name).

1. Additional Non Volatile Phenylated Silicone Oil Having at Least a Dimethicone Part The non volatile phenylated silicone oil having at least a dimethicone part can also be called a non volatile "phenyl dimethicone oil".

According to a first embodiment, the additional non volatile phenylated silicone oil having at least a dimethicone part may be chosen from a) to f) below.

a) The phenyl silicone oils corresponding to the following formula (IV):

$$\text{X—Si(Me)(Me)—[O—Si(Me)(Me)]}_y\text{—O—Si(Me)(Me)—X} \quad (IV)$$

in which Me represents methyl, y is between 1 and 1,000 and X represents —CH$_2$—CH(CH$_3$)(Ph).

b) The phenyl silicone oils corresponding to formula (V) below:

$$\text{Me—Si(Me)(Me)—[O—Si(Me)(Me)]}_y\text{—[O—Si(OR')(Ph)]}_z\text{—O—Si(CH}_3\text{)}_3 \quad (V)$$

in which Me is methyl and Ph is phenyl, OR' represents a group —OSiMe$_3$ and y ranges between 1 and 1000, and z ranges between 1 and 1000. In particular, y and z are such that compound (V) is a non-volatile oil. Use may be made, for example, of trimethyl siloxyphenyl dimethicone, sold especially under the reference Belsil PDM 1000 sold by the company Wacker.

c) The phenyl silicone oils corresponding to formula (VI) below, and mixtures thereof:

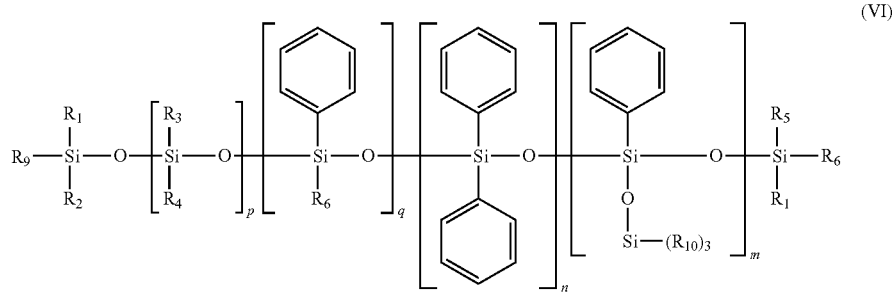

in which:
  $R_1$ to $R_{10}$, independently of each other, are saturated or unsaturated, linear, cyclic or branched $C_1$-$C_{30}$ hydrocarbon-based radicals,
  m, n, p and q are, independently of each other, integers between 0 and 900, p is an integer between 1 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

Preferably, $R_1$ to $R_{10}$, independently of each other, represent a saturated or unsaturated linear or branched $C_1$-$C_{30}$, hydrocarbon radical, preferably saturated, and especially $C_1$-$C_{12}$ hydrocarbon-based radical, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical. Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may especially be identical, and in addition may preferably be a methyl radical.

d) The phenyl silicone oils corresponding to formula (VII) below, and mixtures thereof:

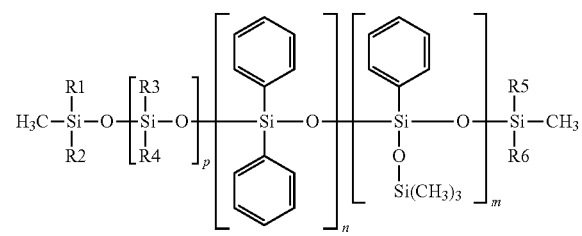

in which:
  $R_1R_2$, $R_5$ and $R_6$, independently of each other, are saturated or unsaturated, linear, cyclic or branched $C_1$-$C_{30}$ hydrocarbon-based radicals, preferably are a $C_1$-$C_{30}$ alkyl radical, an aryl radical or an aralkyl radical,
  $R_3$ and $R_4$ are independently of each other $C_1$-$C_{30}$ hydrocarbon-based alkyl radicals, preferably methyl,
  p is an integer between 1 and 100,
  m and n are, independently of each other, integers between 0 and 100, with the proviso that the sum n+m is between 1 and 100.

Preferably, $R_1R_2$, $R_5$ and $R_6$, independently of each other, represent a saturated or unsaturated linear or branched $C_1$-$C_{30}$, hydrocarbon radical, preferably saturated, and especially $C_1$-$C_{12}$ hydrocarbon-based radical, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical. Preferably, $R_1R_2$, $R_5$ and $R_6$ may each represent a methyl, ethyl, propyl, butyl, isopropyl, decyl, dodecyl or octadecyl radical, or alternatively a phenyl, tolyl, benzyl or phenethyl radical.

$R_1R_2$, $R_5$ and $R_6$ may especially be identical, and in addition may be a methyl radical. Preferably, m=1 or 2 or 3, and/or n=0 may apply, in formula (VII).

e) The phenyl silicone oils corresponding to the following formula, and mixtures thereof:

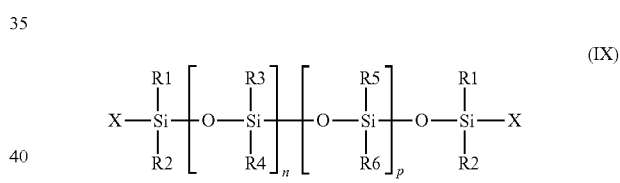

in which:
  $R_1$, $R_2$, $R_5$ and $R_6$ are, together or separately, an alkyl radical containing 1 to 6 carbon atoms,
  $R_3$ and $R_4$ are, together or separately, an alkyl radical containing from 1 to 6 carbon atoms or an aryl radical, with the proviso that at least one from $R_3$ and $R_4$ is a phenyl radical,
  X is an alkyl radical containing from 1 to 6 carbon atoms, a hydroxyl radical or a vinyl radical,
  n and p being integer superior or equal to 1, chosen so as to give the oil a weight-average molecular mass of less than 200 000 g/mol, preferably less than 150 000 g/mol and more preferably less than 100 000 g/mol.

f) And mixture thereof.

Preferably, the weight-average molecular weight of the additional non-volatile phenyl silicone oil having at least a dimethicone part according to the invention ranges from 500 to 10 000 g/mol.

Preferably, the additional non volatile phenylated silicone oil having at least a dimethicone part is chosen from phenyl dimethicone oil corresponding to formula (VII):

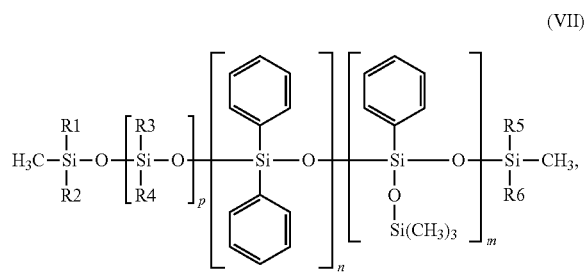

(VII)

wherein $R_1$ to $R_6$, m, n and p, are as defined before.

A) According to a first embodiment, m=0 and n and p are independently of each other, integers between 1 and 100, in formula (VII). Preferably R1 to R6 are methyl radicals. According to this embodiment, the silicone oil is preferably chosen from diphenyl dimethicone such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt).

B) According to a second embodiment, p is between 1 and 100 in formula (VII), the sum m is between 1 and 100, and n=0, in formula (VII). As silicone oils of formula (VII) wherein n=0 and $R_1$ to $R_6$ are methyl radicals, it is especially possible to use a silicone oil chosen from trimethylsiloxyphenyl dimethicone such as Belsil PDM 1000 from Wacker.

Preferably, the additional non-volatile silicone oils having at least a dimethicone part, are chosen from: trimethylsiloxyphenyl dimethicone (for instance Belsil PDM 1000 from the company Wacker (cf. formula (V) above)), phenyl dimethicones, phenyltrimethylsiloxydiphenylsiloxanes, diphenyl dimethicones (such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt).

According to a first preferred embodiment, the additional non volatile silicon oil is a phenyl silicone oil having at least a dimethicone part, and is preferably chosen from:

diphenyl dimethicone such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt);

trimethyl siloxyphenyl dimethicone, such as Belsil PDM 1000 from Wacker, trimethylsiloxyphenyltrimethicone, and mixture thereof.

2. Additional Non Volatile Phenylated Silicon Oil Having No Dimethicone Part

According to one second embodiment variant, a composition according to the invention contains at least one additional non-volatile phenylated silicone oil having no dimethicone part.

The expression "phenylated silicone oil" or "phenyl silicone oil" means a silicone oil having at least one phenyl substituent.

The additional non volatile phenylated silicone oil having no dimethicone part may be chosen from a) to f) below.

a) The phenyl silicone oils corresponding to the following formula (I):

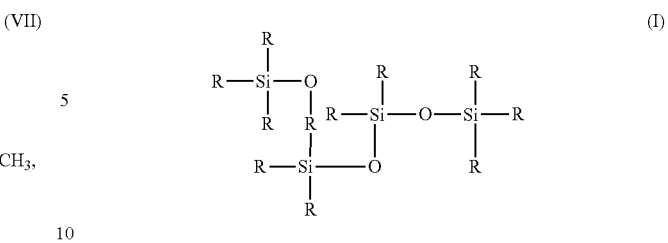

(I)

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

b) The phenyl silicone oils corresponding to the following formula (II):

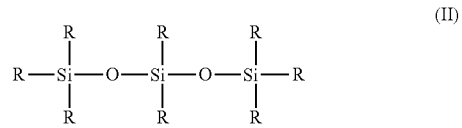

(II)

in which the groups R represent, independently of each other, a methyl or a phenyl, with the proviso that at least one group R represents a phenyl. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.

c) The phenyl silicone oils corresponding to the following formula (III):

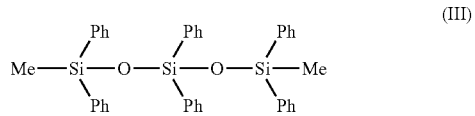

(III)

in which Me represents methyl, Ph represents phenyl.

Such a phenyl silicone oil is preferably trimethyl pentaphenyl trisiloxane, or Tetramethyl Tetraphenyl Trisiloxane. Such oils are especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane), or Tetramethyl Tetraphenyl Trisiloxane sold under the reference Dow Corning 554 Cosmetic Fluid by Dow Corning may also be used.

d) The phenyl silicone oils corresponding to formula (V') below:

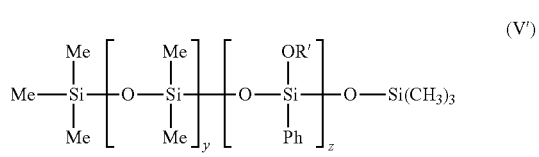

(V')

in which Me is methyl and Ph is phenyl, OR' represents a group —OSiMe$_3$ and y is 0 and z ranges between 1 and 1000, in particular, z is such that compound (V') is a non-volatile oil.

According to a second embodiment, y is equal to 0. Use may be made, for example, of phenyl trimethylsiloxy trisiloxane, sold especially under the reference Dow Corning 556 Cosmetic Grade Fluid (DC556),
e) The phenyl silicone oils corresponding to formula (VIII) below, and mixtures thereof:

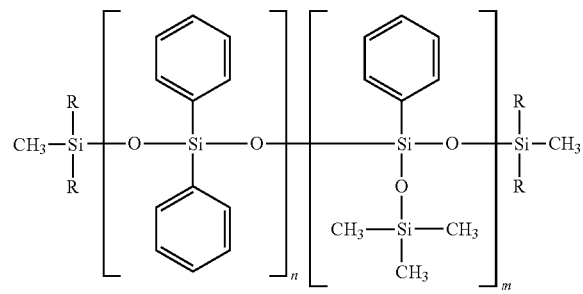

(VIII)

in which:
R, independently of each other, are saturated or unsaturated, linear, cyclic or branched $C_1$-$C_{30}$ hydrocarbon-based radicals, preferably R is a $C_1$-$C_{30}$ alkyl radical, an aryl radical or an aralkyl radical,
m and n are, independently of each other, integers between 0 and 100, with the proviso that the sum n+m is between 1 and 100.

Preferably, R, independently of each other, represent a saturated or unsaturated linear or branched $C_1$-$C_{30}$, hydrocarbon radical, preferably saturated, and especially $C_1$-$C_{12}$ hydrocarbon-based radical, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical. Preferably, R may each represent a methyl, ethyl, propyl, butyl, isopropyl, decyl, dodecyl or octadecyl radical, or alternatively a phenyl, tolyl, benzyl or phenethyl radical. R may especially be identical, and in addition may be a methyl radical. Preferably, m=1 or 2 or 3, and/or n=0 may apply, in formula (VIII).

According to a preferred embodiment, n is an integer between 0 and 100 and m is an integer between 1 and 100, with the proviso that the sum n+m is between 1 and 100, in formula (VIII). Preferably R is methyl radical.

According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used.

According to this embodiment, the non volatile phenyl silicone oil is preferably chosen from phenyl trimethicones; such as DC556 from Dow Corning (22.5 cSt), the oil diphenylsiloxy phenyltrimethicone such as KF56 A from Shin Etsu, the oil Silbione 70663V30 from Rhône-Poulenc (28 cSt). The values in parentheses represent the viscosities at 25° C.

According to this embodiment, when n=0, said silicone oil is preferably DC556 from Dow Corning, and when m and n are between 1 and 100, said said silicone oil is preferably KF56 A from Shin Etsu.
f) And mixture thereof.

According to a second embodiment, the additional silicone oil is a phenyl silicone oil having no dimethicone part, preferably chosen from:
phenyl trimethylsiloxy trisiloxane, phenyl trimethicones; such as DC556 from Dow Corning,
Tetramethyl Tetraphenyl Trisiloxane, such as PH-1554 HRI or Dow Corning 554 Cosmetic Fluid from Dow Corning,
diphenylsiloxy phenyltrimethicone such as KF56 A from Shin Etsu, the oil Silbione 70663V30 from Rhône-Poulenc,
trimethyl pentaphenyl trisiloxane such as PH-1555 HRI or Dow Corning 555 Cosmetic Fluid from Dow Corning, and
mixture thereof.

As preferred additional non-volatile silicone oils, different from said non volatile non phenylated dimethicone oil, examples that may be mentioned include silicone oils such as:
non volatile phenyl silicone oil with no dimethicone part, preferably chosen from: Tetramethyl Tetraphenyl Trisiloxane (such as as PH-1554 HRI or Dow Corning 554 Cosmetic Fluid from Dow Corning), phenyl trimethicones (such as the phenyl trimethicone sold under the trade name DC556 by Dow Corning), phenyltrimethylsiloxydiphenylsiloxanes, diphenylmethyldiphenyltrisiloxanes, 2-phenylethyl trimethylsiloxysilicates, trimethylpentaphenyl trisiloxane (such as the product sold under the name Dow Corning PH-1555 HRI Cosmetic fluid by Dow Corning) (cf. formula (III) above), diphenylsiloxy phenyltrimethicone (such as KF56 A from Shin Etsu),
non volatile phenyl silicone oil having at least a dimethicone part, and
mixtures thereof.

The composition according to the invention may contain from 0.1% to 50% by weight, in particular from 1% to 30% by weight and preferably from 2% to 20% by weight in total of additional non volatile phenylated silicone oil(s), relative to the total weight of the composition.

Preferably, the composition according to the invention comprises no additional non volatile phenylated silicon oil, different from said non volatile non phenylated dimethicone oil.

Non Volatile Hydrocarbonated Apolar Oil:

The composition according to the invention comprises at least one non volatile apolar hydrocarbonated oil (also called apolar "hydrocarbon-based" oil).

More particularly, the composition according to the invention comprises from 1% to 80% by total weight of non volatile hydrocarbonated apolar oil(s), relative to the total weight of the composition.

For the purposes of the present invention, the term "apolar oil" means an oil whose solubility parameter at 25° C., $δ_a$, is equal to 0 (J/cm$^3$)$^{1/2}$.

The definition and calculation of the solubility parameters in the Hansen three-dimensional solubility space are described in the article by C. M. Hansen: "The three dimensional solubility parameters", J. Paint Technol. 39, 105 (1967).

According to this Hansen space:
$δ_D$ characterizes the London dispersion forces derived from the formation of dipoles induced during molecular impacts;
$δ_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

The term "hydrocarbon-based oil" (or "hydrocarbonated oil", or "hydrocarbon oil") means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

These oils may be of plant, mineral or synthetic origin.

Preferably, the non-volatile apolar hydrocarbon-based oil may be chosen from linear or branched hydrocarbons of mineral or synthetic origin.

In particular said-volatile apolar hydrocarbon-based oil may be chosen from:

liquid paraffin or derivatives thereof, squalane, isoeicosane, naphthalene oil, polybutylenes such as Indopol H-100 (molar mass or MW=965 g/mol), Indopol H-300 (MW=1340 g/mol) and Indopol H-1500 (MW=2160 g/mol) sold or manufactured by the company Amoco, polyisobutenes, hydrogenated polyisobutylenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), or alternatively Parleam Lite sold by NOF Corporation, decene/butene copolymers, polybutene/polyisobutene copolymers, especially Indopol L-14, polydecenes and hydrogenated polydecenes such as: Puresyn 10 (MW=723 g/mol) and Puresyn 150 (MW=9200 g/mol) sold or manufactured by the company Mobil Chemicals, or alternatively Puresyn 6 sold by ExxonMobil Chemical), and mixtures thereof.

Preferably, the composition according to the invention comprises at least one non volatile hydrocarbon-based apolar oil, preferably chosen from polybutenes, polyisobutenes, hydrogenated polyisobutenes, polydecenes and/or hydrogenated polydecenes, and mixtures thereof.

A composition according to the invention may comprise a content of non volatile apolar hydrocarbonated oil(s) ranging from 1% to 80%, for example from 2% to 70% by weight and preferably from 5% to 60% by weight, relative to the total weight of the composition.

Preferably said non volatile apolar hydrocarbonated oil comprise at least a hydrogenated polydecene and/or hydrogenated polyisobutene, preferably in a total content ranging from 1 to 80%, preferably from 2 to 70% by weight, relative to the total weight of the composition.

Preferably said non volatile hydrocarbon oil comprise at least a hydrogenated polydecene and/or hydrogenated polyisobutene, preferably in a total content ranging from 5 to 60%, preferably from 10 to 50% by weight, relative to the total weight of the composition.

Preferably, the weight ratio of the total apolar non volatile hydrocarbonated oil(s) to the total non volatile non phenylated dimethicone oil(s) is between 0.2 and 10.

More preferably, the weight ratio of the total apolar non volatile hydrocarbonated oil(s) to the total non volatile phenyl dimethicone oil(s) is between between 0.5 and 8.

More preferably, the weight ratio of the total apolar non volatile hydrocarbonated oil(s) to the total non volatile phenyl dimethicone oil(s) is between 0.8 and 3.

Preferably, the weight ratio of the total non volatile non phenylated dimethicone oil(s) to the total non volatile hydrocarbonated oil(s) to is between 0.6 and 2.5 preferably between 1.5 and 2.2, and even more preferably between 1.5 and 2.

The composition according to the invention may also comprises at least one additional compound, preferably chosen from a hydrocarbonated polar oil, and/or an additional non volatile silicone oil, different from said non phenylated silicon oil having at least a dimethicone part, and/or a fatty pasty compound, and/or a semi-crystalline polymer, and/or a filler, and/or a colouring agent, and/or mixture thereof.

Non Volatile Hydrocarbonated Polar Oil

According to a preferred embodiment, the composition according to the invention comprises an additional non volatile polar hydrocarbonated oil.

For the purposes of the present invention, the term "polar oil" means an oil whose solubility parameter at 25° C., $\delta_a$, is other than 0 $(J/cm^3)^{1/2}$.

These oils may be of plant, mineral or synthetic origin.

In particular, the additional hydrocarbon-based non-volatile polar oil may be chosen from the list of oils below, and mixtures thereof:

hydrocarbon-based plant oils such as liquid triglycerides of fatty acids containing from 4 to 10 carbon atoms, for instance heptanoic or octanoic acid triglycerides or jojoba oil;

ester oils, preferably chosen from:

fatty acid esters, in particular of 4 to 22 carbon atoms, and especially of octanoic acid, heptanoic acid, lanolic acid, oleic acid, lauric acid or stearic acid, for instance propylene glycol dioctanoate, propylene glycol monoisostearate or neopentyl glycol diheptanoate;

synthetic esters, for instance the oils of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 16$, for instance purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate; preferably, the preferred synthetic esters $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms are such that $R_1$ and $R_2 \geq 20$;

linear fatty acid esters with a total carbon number ranging from 35 to 70, for instance pentaerythrityl tetrapelargonate (MW=697 g/mol);

hydroxylated esters, preferably with a total carbon number ranging from 35 to 70, for instance polyglyceryl-2 triisostearate (MW=965 g/mol), isostearyl lactate, octyl hydroxystearate, octyldodecyl hydroxystearate, diisostearyl malate, glyceryl stearate; diethylene glycol diisononanoate;

esters of aromatic acids and of alcohols comprising 4 to 22 atoms, such as tridecyl trimellitate (MW=757 g/mol);

$C_{24}$-$C_{28}$ esters of branched fatty alcohols or fatty acids such as those described in patent application EP-A-0 955 039, and especially triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl) tetradecanoate (MW=1538 g/mol), polyesters resulting from the esterification of at least one hydroxylated carboxylic acid triglyceride with an aliphatic monocarboxylic acid and with an aliphatic dicarboxylic acid, which is optionally unsaturated, for instance the succinic acid and isostearic acid castor oil sold under the reference Zenigloss by Zenitech;

esters of a diol dimer and of a diacid dimer of general formula HO—$R^1$—(—OCO—$R^2$—COO—$R^1$—)$_h$—OH, in which:

$R^1$ represents a diol dimer residue obtained by hydrogenation of dilinoleic diacid, $R^2$ represents a hydrogenated dilinoleic diacid residue, and h represents an integer ranging from 1 to 9, especially the esters of dilinoleic diacids and of dilinoleyl diol dimers sold by the company Nippon Fine Chemical under the trade names Lusplan DD-DA5® and DD-DA7®, polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or copolymers of polyols and of diacid dimers, and esters thereof, such as Hailuscent ISDA;

fatty alcohols containing from 12 to 26 carbon atoms, which are preferably branched, for instance octyldodecanol, 2-butyloctanol, 2-hexyldecanol, 2-undecylpentadecanol and oleyl alcohol;

$C_{12}$-$C_{22}$ higher fatty acids, such as oleic acid, linoleic acid and linolenic acid, and mixtures thereof;

oils of plant origin, such as sesame oil (820.6 g/mol);

fatty acids containing from 12 to 26 carbon atoms, for instance oleic acid;

dialkyl carbonates, the two alkyl chains possibly being identical or different, such as dicaprylyl carbonate sold under the name Cetiol CC® by Cognis; and vinylpyrrolidone copolymers such as the vinylpyrrolidone/1-hexadecene copolymer, Antaron V-216 sold or manufactured by the company ISP (MW=7300 g/mol).

Preferably, the composition according to the invention comprises at least one additional non-volatile polar hydrocarbon oil chosen from:

vinylpyrrolidone copolymers, preferably such as the vinylpyrrolidone/1-hexadecene copolymer;

hydroxylated esters, preferably with a total carbon number ranging from 35 to 70, preferably chosen from polyglyceryl-2 triisostearate, isostearyl lactate, octyl hydroxystearate, octyldodecyl hydroxystearate, diisostearyl malate, glyceryl stearate; diethylene glycol diisononanoate;

oils from plant origin preferably chosen from liquid triglycerides of fatty acids;

$C_{24}$-$C_{28}$ esters of branched fatty alcohols or fatty acids preferably chosen from triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl) tetradecanoate (MW=1538 g/mol);

synthetic esters of formula $R_1COOR_2$ in which $R_1$ represents a linear or branched fatty acid residue containing from 4 to 40 carbon atoms and $R_2$ represents a hydrocarbon-based chain that is especially branched, containing from 4 to 40 carbon atoms, provided that $R_1+R_2 \geq 16$; and mixtures thereof.

A composition according to the invention may comprise a content of additional non volatile polar hydrocarbonated oil ranging from 1% to 80%, for example from 2% to 70% by weight and preferably from 5% to 60% by weight, relative to the total weight of the composition.

A composition according to the invention may comprise a content of additional non volatile polar hydrocarbonated oil ranging from 5% to 60% by weight, preferably from 10 to 50% by weight, relative to the total weight of the composition.

Preferably, the weight ratio of the total non volatile hydrocarbonated oil(s) (ie apolar and polar oils) to the total non volatile non silicone oil(s) comprised between 0.1 and 20, more preferably comprised between 0.2 and 10, and preferably comprised between 1 and 5.

A cosmetic makeup and/or care composition according to the invention also comprises a cosmetically acceptable medium that may comprise the usual ingredients, as a function of the intended use of the composition.

Additional Fatty Phase

According to one embodiment, the composition according to the invention may comprise, besides said non volatile silicone oil and said non volatile hydrocarbonated oil, an additional liquid fatty phase, preferably chosen from non volatile polar hydrocarbonated oils described before, and/or non volatile silicone oils, different from said non phenylated dimethicone oils, as described before.

The additional liquid fatty phase may represent from 0.1% to 80% by weight relative to the total weight of the composition.

In particular, a composition according to the invention and/or used in a composition according to the invention may comprise from 0.1% to 75% by weight of an additional liquid fatty phase relative to its total weight.

More particularly, a composition according to the invention and/or used in a composition according to the invention may comprise from 0.5% to 70% by weight of an additional liquid fatty phase relative to its total weight.

Volatile Oil

According to one embodiment, the composition according to the invention may comprise a volatile oil.

Thus, a composition under consideration according to the invention may advantageously comprise one or more oils, which may be chosen especially from volatile hydrocarbon-based oils, volatile silicone oil and fluoro oils, and mixtures thereof.

For the purposes of the invention, the term "volatile oil" means an oil that is capable of evaporating on contact with keratin materials in less than one hour, at room temperature (25° C.) and atmospheric pressure (760 mmHg). The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.1 to 10 mmHg).

The oils may be of animal, plant, mineral or synthetic origin.

Volatile Fluoro Oil

The term "fluoro oil" means an oil comprising at least one fluorine atom.

The fluoro oils that may be used in the invention may be chosen from fluorosilicone oils, fluoro polyethers and fluorosilicones as described in document EP-A-847 752, and perfluoro compounds.

According to the invention, the term "perfluoro compounds" means compounds in which all the hydrogen atoms have been replaced with fluorine atoms.

According to one preferred embodiment, the fluoro oil according to the invention is chosen from perfluoro oils. As examples of perfluoro oils that may be used in the invention, mention may be made of perfluorodecalins and perfluoroperhydrophenanthrenes.

According to one preferred embodiment, the fluoro oil is chosen from perfluoroperhydrophenanthrenes, and especially the Fiflow® products sold by the company Creations Couleurs. In particular, use may be made of the fluoro oil whose INCI name is perfluoroperhydrophenanthrene, sold under the reference Fiflow 220 by the company F2 Chemicals.

Volatile Hydrocarbon Oil

According to a preferred embodiment, the composition according to the invention further comprises a volatile hydrocarbonated oil such as isododecane and/or isohexadecane.

Such compound is compatible with the non volatile hydrocarbonated and silicone oil and improve the spreadability during application and the transfer resistance of the deposit.

The term "hydrocarbon-based oil" (or "hydrocarbonated oil", or "hydrocarbon oil") means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The volatile hydrocarbon-based oils may be chosen from hydrocarbon-based oils containing from 8 to 16 carbon atoms, and especially $C_8$-$C_{16}$ branched alkanes (also known as isoparaffins), for instance isododecane (also called 2,2,4,4,6-pentamethylheptane), isodecane and isohexadecane, and mixture thereof.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

The term "hydrocarbon-based oil" is intended to mean an oil formed essentially, or even constituted, of carbon and hydrogen atoms, and optionally of oxygen and nitrogen atoms, and containing no silicon or fluorine atoms. It may contain alcohol, ester, ether, carboxylic acid, amine and/or amide groups.

According to one embodiment, a composition according to the invention also comprises at least isododecane and/or isohexadecane.

According to one embodiment, the composition is free of additional volatile hydrocarbonated oil other than isododecane and/or isohexadeCane.

More particularly, the composition according to the invention contains between 0.1% and 20% by weight of volatile oil, preferably isododecane and/or isohexadecane, relative to its total weight.

Preferably, the composition according to the invention contains between 1% and 15% by weight of volatile oil, preferably of isododecane and/or isohexadecane, relative to its total weight.

Advantageously, the composition according to the invention contains between 1% and 10% by weight of volatile oil, preferably of isododecane and/or isohexadecane, relative to its total weight.

As other volatile hydrocarbon-based solvents (oils) that can be used in the composition according to the invention, mention may also be made of ketones which are liquid at ambient temperature, such as methyl ethyl ketone or acetone; short-chain esters (containing from 3 to 8 carbon atoms in total), such as ethyl acetate, methyl acetate, propyl acetate or n-butyl acetate; ethers which are liquid at ambient temperature, such as diethyl ether, dimethyl ether or dichlorodiethyl ether; alcohols, and in particular linear or branched lower monoalcohols containing from 2 to 5 carbon atoms, for instance ethanol, isopropanol or n-propanol.

According to one preferred embodiment, the volatile oil has a flash point of greater than 65° C., and better still greater than 80° C. By way of example of such a volatile oil, mention may be made of isohexadecane.

Advantageously, the composition according to the invention comprises less than 5% and better still less than 2% by weight of volatile oil having a flash point of less than 80° C., relative to the total weight of the composition. Preferably, the composition according to the invention is free of volatile oil having a flash point of less than 80° C.

Volatile Silicone Oils

According to an embodiment, the compositions according to the invention may comprise at least one volatile silicone oil.

The term "silicone oil" is intended to mean an oil comprising at least one silicon atom, and in particular comprising Si—O groups.

The volatile silicone oil that may be used in the invention may be chosen from silicone oils especially having a viscosity 8 centistokes (cSt) ($8 \times 10^{-6}$ $m^2/s$) and preferably greater than 0.5 cSt.

The term "silicone oil" is intended to mean an oil comprising at least one silicon atom, and in particular comprising Si—O groups.

The volatile silicone oil that can be used in the invention may be chosen from silicone oils having a flash point ranging from 40° C. to 150° C., preferably having a flash point of greater than 55° C. and less than or equal to 105° C., and preferentially ranging from 65° C. to 95° C. The flash point is in particular measured according to ISO standard 3679.

The volatile silicone oil may be chosen from linear or cyclic silicone oils such as linear or cyclic polydimethylsiloxanes (PDMSs) having from 3 to 7 silicon atoms.

Volatile silicone oils that may more particularly be mentioned include decamethylcyclopentasiloxane sold especially under the name DC-245 by the company Dow Corning, dodecamethylcyclohexasiloxane sold especially under the name DC-246 by the company Dow Corning, octamethyltrisiloxane sold especially under the name DC-200 Fluid 1 cSt by the company Dow Corning, polydimethylsiloxanes such as decamethyltetrasiloxane sold especially under the name DC-200 Fluid 1.5 cSt by the company Dow Corning and DC-200 Fluid 5 cSt sold by the company Dow Corning, octamethylcyclotetrasiloxane, heptamethyihexyltrisiloxane, heptamethylethyltrisiloxane, heptamethyloctyltrisiloxane and dodecamethylpentasiloxane, octyl trimethicone, hexyl trimethicone, decamethylcyclopentasiloxane (cyclopentasiloxane or D5), octamethylcyclotetrasiloxane (cyclotetradimethylsiloxane or D4), dodecamethylcyclohexasiloxane (D6), decamethyltetrasiloxane (L4), KF 96 A from Shin Etsu, and mixtures thereof.

According to a preferred embodiment, the composition according to the invention is free from volatile oil.

Solid Fatty Substances

A composition according to the invention may preferably also comprise at least one solid fatty substance especially chosen from waxes and/or pasty fatty substances.

Waxes

According to a first preferred embodiment, the composition is free of wax or contains less than 5% by weight of waxes, preferably less than 3%, relative to the total weight of the composition.

Advantageously, according to this embodiment, the composition is liquid at room temperature. In particular, in case a makeup composition, for instance for the lips, the composition can be a lipgloss.

According to a second embodiment, the composition comprises at least one wax. According to this embodiment, preferably, the amount of wax(es) in the makeup and/or care composition according to the invention is between 0.5% and 30% by weight, especially from 1% to 20% by weight or even 2% to 15% by weight, relative to the total weight of the composition.

In particular, the presence of waxes is preferred when the composition according to the invention is solid at room temperature. In particular, in case a makeup composition, for instance for the lips, the composition can be a lipsticks.

The term "wax" means a lipophilic compound that is solid at room temperature (25° C.), with a reversible solid/liquid change of state, having a melting point of greater than or equal to 30° C., which may be up to 200° C. The waxes may be chosen from waxes of animal, plant, mineral or synthetic origin, and mixtures thereof. Mention may be made especially of hydrocarbon-based waxes, for instance beeswax, lanolin wax and Chinese insect waxes; rice bran wax, carnauba wax, candelilla wax, ouricury wax, alfalfa wax, berry wax, shellac wax, Japan wax and sumach wax; montan wax, orange wax, lemon wax, microcrystalline waxes, paraffins and ozokerite; polyethylene waxes, the waxes obtained by Fisher-Tropsch synthesis and waxy copolymers, and also esters thereof. Mention may also be made of waxes obtained by catalytic hydrogenation of animal or plant oils containing linear or branched $C_8$-$C_{32}$ fatty chains. Among these, mention may be made especially of hydrogenated sunflower oil, hydrogenated castor oil, hydrogenated coconut oil, hydrogenated lanolin oil and bis(1,1,1-trimethylolpropane)tetrastearate. Mention may also be made of silicone waxes and fluoro waxes. The waxes obtained by hydrogenation of castor oil esterified with cetyl alcohol may also be used.

Advantageously, a composition according to the invention may comprise at least one wax, especially a hydrocarbon-based wax.

Pasty Fatty Substances

According to a first embodiment, the composition is free of pasty fatty substances.

According to a second preferred embodiment, the composition comprises at least one pasty fatty substance. According to this embodiment, preferably, the amount of pasty fatty substance in the makeup and/or care composition according to the invention is between 0.5% and 60% by weight, especially from 1% to 50% by weight or even 2% to 40% by weight, relative to the total weight of the composition.

The term "pasty", within the meaning of the present invention, is understood to mean a lipophilic fatty compound with a reversible solid/liquid change of state exhibiting, in the solid state, an anisotropic crystalline arrangement and comprising, at a temperature of 23° C., a liquid fraction and a solid fraction.

The term "pasty compound", within the meaning of the invention, is understood to mean a compound having a hardness at 20° C. ranging from 0.001 to 0.5 MPa, preferably from 0.002 to 0.4 MPa.

The hardness is measured according to a method of penetration of a probe into a sample of compound and in particular using a texture analyser (for example, the TA-XT2i from Rheo) equipped with a stainless steel cylinder with a diameter of 2 mm. The hardness measurement is carried out at 20° C. at the centre of 5 samples. The cylinder is introduced into each sample at a pre-rate of 1 mm/s and then at a measuring rate of 0.1 mm/s, the depth of penetration being 0.3 mm. The value recorded for the hardness is that of the maximum peak.

In addition, this pasty compound is, at a temperature of 23° C., in the form of a liquid fraction and of a solid fraction. In other words, the starting melting temperature of the pasty compound is less than 23° C. The liquid fraction of the pasty compound, measured at 23° C., represents 9 to 97% by weight of the compound. This liquid fraction at 23° C. preferably represents between 15 and 85%, more preferably between 40 and 85%, by weight.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound to change from the solid state to the liquid state. The pasty compound is "in the solid state" when the whole of its mass is in the crystalline solid form. The pasty compound is "in the liquid state" when the whole of its mass is in the liquid form.

The enthalpy of fusion of the pasty compound is equal to the area under the curve of the thermogram obtained using a differential scanning calorimeter (DSC), such as the calorimeter sold under the name MDSC 2920 by TA Instrument, with a rise in temperature of 5 or 10° C. per minute, according to the ISO Standard 11357-3: 1999. The enthalpy of fusion of the pasty compound is the amount of energy necessary to change the compound from the solid state to the liquid state. It is expressed in J/g.

The enthalpy of fusion consumed at 23° C. is the amount of energy absorbed by the sample to change from the solid state to the state which it exhibits at 23° C., composed of a liquid fraction and of a solid fraction.

The liquid fraction of the pasty compound measured at 32° C. preferably represents from 30 to 100% by weight of the compound, preferably from 80 to 100%, more preferably from 90 to 100%, by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound is preferably chosen from synthetic compounds and compounds of plant origin. A pasty compound may be obtained by synthesis from starting materials of plant origin. Mention may be made especially, alone or as a mixture, of:

The pasty fatty substance is advantageously chosen from:
lanolin, and derivatives thereof, such as lanolin alcohol, oxyethylenated lanolins, acetylated lanolin, lanolin esters such as isopropyl lanolate, and oxypropylenated lanolins, petroleum jelly, in particular the product whose INCI name is petrolatum and which is sold under the name Ultima White PET USP by the company Penreco, polyol ethers chosen from polyalkylene glycol pentaerythrityl ethers, fatty alcohol ethers of sugars, and mixtures thereof, polyethylene glycol pentaerythrityl ether comprising five oxyethylene (5 OE) units (CTFA name: PEG-5 Pentaerythrityl Ether), polypropylene glycol pentaerythrityl ether comprising five oxypropylene (5 OP) units (CTFA name: PEG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil;

polymeric or non-polymeric silicone compounds;
polymeric or non-polymeric fluoro compounds;
vinyl polymers, especially:
olefin homopolymers and copolymers,
hydrogenated diene homopolymers and copolymers,
linear or branched oligomers, homopolymers or copolymers of alkyl (meth)acrylates preferably containing a $C_8$-$C_{30}$ alkyl group,
oligomers, homopolymers and copolymers of vinyl esters containing $C_8$-$C_{30}$ alkyl groups,
oligomers, homopolymers and copolymers of vinyl ethers containing $C_8$-$C_{30}$ alkyl groups, liposoluble polyethers resulting from the polyetherification between one or more $C_2$-$C_{100}$ and preferably $C_2$-$C_{50}$ diols, esters (ie pasty fatty substance comprising at least one ester function); and/or
mixtures thereof.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Preferably, the pasty fatty substance comprises at least one ester function. Among the ester pasty fatty substances, the following are especially preferred:

esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, preferably such as bis-diglyceryl polyacyladipate-2 sold under the brand name Softisan 649 by the company Sasol, vinyl ester homopolymers containing $C_8$-$C_{30}$ alkyl groups, such as polyvinyl laurate (sold especially under the reference Mexomer PP buy the company Chimex) and arachidyl propionate sold under the brand name Waxenol 801 by Alzo, phytosterol esters, fatty acid triglycerides and derivatives thereof, for instance triglycerides of fatty acids, which are especially $C_{10}$-$C_{18}$, and partially or totally hydrogenated such as those sold under the reference Softisan 100 by the company Sasol, pentaerythritol esters, non-crosslinked polyesters resulting from polycondensation between a linear or branched $C_4$-$C_{50}$ dicarboxylic acid or polycarboxylic acid and a $C_2$-$C_{50}$ diol or polyol, aliphatic esters of an ester resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:

a) partial or total esters of saturated linear mono-hydroxylated aliphatic monocarboxylic acids;
b) partial or total esters of unsaturated monohydroxylated aliphatic monocarboxylic acids;
c) partial or total esters of saturated monohydroxylated aliphatic polycarboxylic acids;
d) partial or total esters of saturated poly-hydroxylated aliphatic polycarboxylic acids;
e) partial or total esters of $C_2$ to $C_{16}$ aliphatic polyols that have reacted with a monohydroxylated or polyhydroxylated aliphatic monocarboxylic or poly-carboxylic acid, and mixtures thereof, esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (commercialised under the references Plandool G and Plandool G7), phytosteryl/isostearyl/stearyl/behenyl dimer dilinoleate (Plandool H or Plandool S), and mixtures thereof, esters obtained by allowing a monohydric alcohol having 1 to 34 carbon atoms to react with an ester which is obtained by reacting a dimer acid with an alcohol mixture of a dimer diol and a trihydric or higher hydric alcohol having 3 to 10 carbon atoms, by using 0.8 to 1.5, preferably 0.4 to 0.8, and even more preferably 0.2 to 3.5, molar equivalent(s) of the monohydric alcohol with respect to one molar equivalent of a carboxyl group remaining in the ester obtained from the dimer acid and the alcohol mixture.

The dimer acid can be obtained by standardized industrial processes. More particularly, the dimer acid can be obtained by dimerizing an unsaturated fatty acid with 11 to 22 carbon atoms, or a lower alcohol ester thereof with a clay catalyst or the like. The resulting dimer acid has a dibasic acid having about 36 carbon atoms as a main ingredient, and may contain a trimer acid and a monomer acid in amounts in accordance with the degree of purification. The dimers derived from vegetable fats and oils are preferable. As the aforementioned dimers, for example, PRIPOL 1006, PRIPOL 1009, PRIPOL 1015, and PRIPOL 1025 provided by Croda Inc., and the like, can be used.

The dimer diol is more particularly a product having a diol with about 36 carbon atoms as a main ingredient. The dimer diol is obtained by hydrogenating the aforementioned dimer acid and/or the lower alcohol ester thereof in the presence of a catalyst to form the diol having about 36 carbon atoms in which the carboxylic acid part of the dimer acid is an alcohol. The dimer diols derived from vegetable fats and oils are preferable. For example, PRIPOL 2033 provided by Croda Inc., can be used.

The trihydric or higher hydric alcohol having 3 to 10 carbon atoms is preferably selected from glycerol, diglycerol, trimethylolpropane, pentaerythritol, ditrimethylolpropane and dipentaerythritol.

The monohydric alcohol having 1 to 34 carbon atoms is more particularly selected from a linear saturated alcohol having 12 to 22 carbon atoms, a branched saturated alcohol having 8 to 22 carbon atoms, cholesterol and phytosterol. Preferably, the monohydric alcohol is a linear saturated monohydric alcohol having 16 or more carbon atoms, and is in the form of a paste. According to another embodiment, the monohydric alcohol is cholesterol or phytosterol. In addition, a double bond remains after the dimerization reaction. Therefore, a dimer acid in which hydrogenation is further carried out can be used.

Such products are for instance described in JP 2011-20933 filed in the name of Nippon Fine Chemical Co., Ltd.

mango butter, such as the product sold under the reference Lipex 203 by the company Aarhuskarlshamn, hydrogenated oils of plant origin such as hydrogenated castor oil isostearate (sold as (SALACOS HCIS (V-L) from NISSHIN OIL), hydrogenated soybean oil, hydrogenated coconut oil, hydrogenated rape seed oil, mixtures of hydrogenated plant oils such as the mixture of hydrogenated soybean, coconut, palm and rape seed plant oil, for example the mixture sold under the reference Akogel® by the company Aarhuskarlshamn (INCI name: Hydrogenated Vegetable Oil).

shea butter, in particular the product whose INCI name is Butyrospermum parkii Butter, such as the product sold under the reference Sheasoft® by the company Aarhuskarlshamn, hydrogenated rosinate esters, such as dilinoleyl dimers of hydrogenated rosinate (Lusplan DD-DHR or DD-DHR from Nippon Fine Chemical); and mixtures thereof.

Preferably, the pasty fatty substance, is a hydrocarbon-based compound comprising at least one ester function.

Preferably, the pasty fatty substance, is chosen from hydrogenated castor oil isostearate (SALACOS HCIS (V-L) from NISSHIN OIL), bis-behenyl/isostearyl/phytosteryl dimer dilinoleyl dimer dilinoleate, esters obtained by allowing a monohydric alcohol having 1 to 34 carbon atoms to react with an ester which is obtained by reacting a dimer acid with an alcohol mixture of a dimer diol and a trihydric or higher hydric alcohol having 3 to 10 carbon atoms, by using 0.8 to 1.5 molar equivalent(s) of the monohydric alcohol with respect to one molar equivalent of a carboxyl group remaining in the ester obtained from the dimer acid and the alcohol mixture (and for instance described in JP2011-20933), bis-diglyceryl polyacyladipate-2, hydrogenated castor oil dimer dilinoleate (Risocast-DA-L®, Risocast DA-H®, sold by Kokyu Alcohol Kogyo), polyvinyl laurate, mango butter, shea butter, hydrogenated soybean oil, hydrogenated coconut oil and hydrogenated rape seed oil, and mixtures thereof.

According to a particularly preferred embodiment of the invention, the cosmetic composition for making up and/or caring for the skin and/or the lips, comprising in a physiologically acceptable medium, at least one fatty phase comprising:

at least one hydrocarbon-based resin with a number-average molecular weight of less than or equal to 10 000 g/mol, at least one hydrocarbon-based block polymer, from 11% to 80% by total weight of non volatile non phenylated silicone oil(s) having at least a dimethicone part, or mixture thereof, relative to the total weight of the composition, and from 1% to 80% by weight of non volatile hydrocarbonated apolar oil(s), or mixture thereof, relative to the total weight of the composition;

at least a pasty compound chosen from (i) bis-behenyl/isostearyl/phytosteryl dimer dilinoleyl dimer dilinoleate; (ii) esters obtained by allowing a monohydric alcohol having 1 to 34 carbon atoms to react with an ester which is obtained by reacting a dimer acid with an alcohol mixture of a dimer diol and a trihydric or higher hydric alcohol having 3 to 10 carbon atoms, by using 0.8 to 1.5 molar equivalent(s) of the monohydric alcohol with respect to one molar equivalent of a carboxyl group remaining in the ester obtained from the dimer acid and the alcohol mixture; and preferably among (ii).

Semi-Crystalline Polymer

The composition according to the invention may also comprise a semi-crystalline polymer.

The term "polymers" is understood to mean, within the meaning of the invention, compounds comprising at least 2 repeat units, preferably at least 3 repeat units and more especially at least 10 repeat units.

The term "semi-crystalline polymer" is understood to mean, within the meaning of the invention, polymers comprising a crystallizable part and an amorphous part in the backbone and exhibiting a first-order reversible phase change temperature, in particular a melting point (solid-liquid transition). The crystallizable part is either a side chain (or a pendent chain) or a block in the backbone.

When the crystallizable part of the semi-crystalline polymer is a block of the polymer backbone, this crystallizable block is different in chemical nature from the amorphous blocks; in this case, the semi-crystalline polymer is a block copolymer, for example of the diblock, triblock or multiblock type. When the crystallizable part is a chain pendent to the backbone, the semi-crystalline polymer can be a homopolymer or a copolymer.

The term "organic compound" or "with an organic structure" is understood to mean compounds comprising carbon atoms and hydrogen atoms and optionally heteroatoms, such as S, O, N or P, alone or in combination.

The melting point of the semi-crystalline polymer is preferably less than 150° C.

The melting point of the semi-crystalline polymer is preferably greater than or equal to 30° C. and less than 100° C. Preferably again, the melting point of the semi-crystalline polymer is preferably greater than or equal to 30° C. and less than 60° C.

The semi-crystalline polymer or polymers according to the invention are solids at ambient temperature (25° C.) and atmospheric pressure (760 mmHg), the melting points of which are greater than or equal to 30° C. The melting point values correspond to the melting point measured using a differential scanning calorimeter (DSC), such as the calorimeter sold under the name DSC30 by Mettler, with a rise in temperature of 5 or 10° C. per minute (the melting point considered is the point corresponding to the temperature of the most endothermic peak of the thermogram).

The semi-crystalline polymer or polymers according to the invention preferably have a melting point which is greater than the temperature of the keratinous substrate intended to receive the said composition, in particular the skin or lips.

The semi-crystalline polymer or polymers according to the invention may be capable of structuring, alone or as a mixture, the composition without addition of a specific surfactant or of filler or of wax.

According to the invention, the semi-crystalline polymers are advantageously soluble in the fatty phase, in particular to at least 1% by weight, at a temperature greater than their melting point. Apart from the crystallizable chains or blocks, the blocks of the polymers are amorphous.

The term "crystallizable chain or block" is understood to mean, within the meaning of the invention, a chain or block which, if it were alone, would change reversibly from the amorphous state to the crystalline state, according to whether the temperature is above or below the melting point. A chain within the meaning of the invention is a group of atoms which is in the pendent or side position with respect to the backbone of the polymer. A block is a group of atoms belonging to the backbone, a group constituting one of the repeat units of the polymer.

The polymer backbone of the semi-crystalline polymers is preferably soluble in the fatty phase.

Preferably, the crystallizable blocks or chains of the semi-crystalline polymers represent at least 30% of the total weight of each polymer and better still at least 40%. The semi-crystalline polymers with crystallizable side chains are homo- or copolymers. The semi-crystalline polymers of the invention with crystallizable blocks are block or multiblock copolymers. They can be obtained by polymerization of a monomer with reactive (or ethylenic) double bonds or by polycondensation. When the polymers of the invention are polymers with crystallizable side chains, the latter are advantageously in the statistical or random form.

Preferably, the semi-crystalline polymers of the invention are synthetic in origin. According to one embodiment of the invention, the semi-crystalline polymers of the invention do not comprise a polysaccharide backbone.

The semi-crystalline polymers which can be used in the invention can be chosen in particular from:
  block copolymers of polyolefins with controlled crystallization, the monomers of which are disclosed in EP-A-0 951 897,
  polycondensates and in particular of aliphatic or aromatic or aliphatic/aromatic polyester type,
  homo- or copolymers carrying at least one crystallizable side chain and homo- or copolymers carrying, in the backbone, at least one crystallizable block, such as those disclosed in the document U.S. Pat. No. 5,156,911,
  homo- or copolymers carrying at least one crystallizable side chain with in particular fluorinated group(s), such as disclosed in the document WO-A-01/19333, and
  their mixtures.

In the last two cases, the crystallizable side chain or block or side chains or blocks are hydrophobic.

A) Semi-Crystalline Polymers with Crystallizable Side Chains

According to a first preferred embodiment, the semi-crystalline polymer is chosen from semi-crystalline polymers with crystallizable side chains.

Mention may in particular be made of those defined in the documents U.S. Pat. No. 5,156,911 and WO-A-01/19333.

These are homopolymers or copolymers comprising from 50 to 100% by weight of units resulting from the polymerization of one or more monomers carrying a crystallizable hydrophobic side chain.

These homo- or copolymers can have any nature provided that they exhibit the conditions indicated below, with in particular the characteristic of being soluble or dispersible in the fatty phase by heating above their melting point M.p. They can result:
  from the polymerization, in particular radical polymerization, of one or more monomers with double bond(s) or ethylenic monomers reactive with respect to polymerization, namely with a vinyl, (meth)acrylic or allyl group,
  from the polycondensation of one or more monomers carrying coreactive groups (carboxylic or sulphonic acid, alcohol, amine or isocyanate groups), such as, for example, polyesters, polyurethanes, polyethers, polyureas or polyamides.

Generally, the crystallizable units (chains or blocks) of the semi-crystalline polymers according to the invention originate from monomer(s) with crystallizable block(s) or chain(s) used for the manufacture of semi-crystalline polymers. These polymers are chosen in particular from the homopolymers and copolymers resulting from the polymerization of at least one monomer with crystallizable chain(s) which can be represented by the formula X:

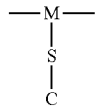

with M representing an atom of the polymer backbone, S representing a spacer, and C representing a crystallizable group.

The crystallizable chains "—S—C" can be aliphatic or aromatic and optionally fluorinated or perfluorinated. "S" represents in particular a linear or branched or cyclic $(CH_2)_n$ or $(CH_2CH_2O)_n$ or $(CH_2O)$ group with n an integer ranging from 0 to 22. Preferably, "S" is a linear group. Preferably, "S" and "C" are different.

When the crystallizable chains are hydrocarbon aliphatic chains, they comprise hydrocarbon alkyl chains with at least 11 carbon atoms and at most 40 carbon atoms and better still at most 24 carbon atoms. They are in particular aliphatic chains or alkyl chains having at least 12 carbon atoms and preferably they are $C_{14}$-$C_{24}$, preferably $C_{16}$-$C_{22}$, alkyl chains. When they are fluorinated or perfluorinated alkyl chains, they comprise at least 11 carbon atoms, at least 6 carbon atoms of which are fluorinated.

Mention may be made, as example of semi-crystalline homopolymers or copolymers with crystallizable chain(s), of those resulting from polymerization of one or more following monomers: saturated alkyl (meth)acrylates with the $C_{14}$-$C_{24}$ alkyl group, perfluoroalkyl (meth)acrylates with a $C_{11}$-$C_{15}$ perfluoroalkyl group, N-alkyl(meth)acrylamides with the $C_{14}$ to $C_{24}$ alkyl group, with or without a fluorine atom, vinyl esters with alkyl or perfluoro(alkyl) chains with the $C_{14}$ to $C_{24}$ alkyl group (with at least 6 fluorine atoms per one perfluoroalkyl chain), vinyl ethers with alkyl or perfluoro(alkyl) chains with the $C_{14}$ to $C_{24}$ alkyl group and at least 6 fluorine atoms per one perfluoroalkyl chain, $C_{14}$ to $C_{24}$ α-olefins, such as, for example, octadecene, para-alkylstyrenes with an alkyl group comprising from 12 to 24 carbon atoms, and their mixtures.

When the polymers result from a polycondensation, the crystallizable hydrocarbon and/or fluorinated chains as defined above are carried by a monomer which can be a diacid, a diol, a diamine or a diisocyanate.

When the polymers which are subject-matters of the invention are copolymers, they additionally comprise from 0 to 50% of Y or Z groups resulting from the copolymerization:

α) of Y, which is a polar or nonpolar monomer or a mixture of the two:
  when Y is a polar monomer, it is a monomer carrying polyoxyalkylenated groups (in particular oxyethylenated and/or oxypropylenated groups), a hydroxyalkyl (meth)acrylate, such as hydroxyethyl acrylate, (meth)acrylamide, an N-alkyl(meth)acrylamide, an N,N-dialkyl(meth)acrylamide, such as, for example, N,N-diisopropylacrylamide or N-vinylpyrrolidone (NVP), N-vinylcaprolactam, or a monomer carrying at least one carboxylic acid group, such as (meth)acrylic acid, crotonic acid, itaconic acid, maleic acid or fumaric acid, or carrying a carboxylic acid anhydride group, such as maleic anhydride, and their mixtures; and
  when Y is a nonpolar monomer, it can be an ester of the linear, branched or cyclic alkyl (meth)acrylate type, a vinyl ester, an alkyl vinyl ether, an α-olefin, styrene or styrene substituted by a $C_1$-$C_{10}$ alkyl group, such as α-methylstyrene, or a macromonomer of the polyorganosiloxane type with vinyl unsaturation. The term "alkyl" is understood to mean, within the meaning of the invention, a saturated group, in particular a $C_8$-$C_{24}$ group, unless specifically mentioned, or β) of Z, which is a polar monomer or a mixture of polar monomers. In this case, Z has the same definition as the "polar Y" defined above.

Preferably, the semi-crystalline polymers with a crystallizable side chain are alkyl (meth)acrylate or alkyl(meth)acrylamide homopolymers with an alkyl group as defined above and in particular a $C_{14}$-$C_{24}$ alkyl group, copolymers of these monomers with a hydrophilic monomer preferably different in nature from (meth)acrylic acid, such as N-vinylpyrrolidone or hydroxyethyl (meth)acrylate, and their mixtures.

Advantageously, the semi-crystalline polymer or polymers with a crystallizable side chain have a weight-average molecular mass $M_w$ ranging from 5000 to 1 000 000, preferably from 10 000 to 800 000, preferentially from 15 000 to 500 000, more preferably from 100 000 to 200 000.

Mention may be made, as specific example of semi-crystalline polymer which can be used in the composition according to the invention, of the Intelimer® products from Landec described in the brochure "Intelimer® polymers", Landec IP22 (Rev. 4-97). These polymers are in the solid form at ambient temperature (25° C.). They carry crystallizable side chains and exhibit the above formula X.

For example, the choice is made of the Intelimer® product IPA 13-1 from Landec, which is a poly(stearyl acrylate) with a molecular weight of approximately 145 000 and a melting point of 49° C.

The semi-crystalline polymers can be in particular those disclosed in examples 3, 4, 5, 7 and 9 of U.S. Pat. No. 5,156,911 comprising a —COOH group, resulting from the copolymerization of acrylic acid and of $C_5$ to $C_{16}$ alkyl (meth)acrylate with a melting point ranging from 20° C. to 35° C. and more particularly from the copolymerization:
  of acrylic acid, of hexadecyl acrylate and of isodecyl acrylate in a 1/16/3 ratio,
  of acrylic acid and of pentadecyl acrylate in a 1/19 ratio,
  of acrylic acid, of hexadecyl acrylate and of ethyl acrylate in a 2.5/76.5/20 ratio,
  of acrylic acid, of hexadecyl acrylate and of methyl acrylate in a 5/85/10 ratio, and
  of acrylic acid and of octadecyl methacrylate in a 2.5/97.5 ratio.

Use may also be made of the polymer Structure "O" from National Starch, such as that disclosed in the document U.S. Pat. No. 5,736,125 with a melting point of 44° C.

The semi-crystalline polymers can be in particular semi-crystalline polymers with crystallizable pendent chains comprising fluorinated groups, such as disclosed in Examples 1, 4, 6, 7 and 8 of the document WO-A-01/19333.

Use may also be made of the semi-crystalline polymers obtained by copolymerization of stearyl acrylate and of acrylic acid or of NVP as disclosed in the document U.S. Pat. No. 5,519,063 or EP-A-0 550 745. Such semi-crystalline polymer is for example the product commercialised under the reference INTELIMER 13-1 by Air Product and Chemicals. The INCI name of such product is POLY C10-30 ALKYL ACRYLATE.

Use may also be made of the semi-crystalline polymers obtained by copolymerization of behenyl acrylate and of acrylic acid or of NVP as disclosed in the documents. Such semi-crystalline polymer is for example the product commercialised under the reference INTELIMER 13-6 by Air Product and Chemicals. The INCI name of such product is POLY C10-30 ALKYL ACRYLATE.

According to a preferred embodiment, the semi-crystalline polymers with crystallizable side chains is chose, from POLY C10-30 ALKYL ACRYLATE, and more particularly from Poly stearyle acrylate and/or poly behenyle acrylate.

B) Polymers Carrying, in the Backbone, at Least One Crystallizable Block

According to a second embodiment, the semi-crystalline polymer is chosen from polymers carrying, in the backbone, at least one crystallizable block.

These are again polymers which are soluble or dispersible in the fatty phase by heating above their melting point M.p. These polymers are in particular block copolymers composed of at least two blocks of different chemical natures, one of which is crystallizable.

The polymer carrying, in the backbone, at least one crystallizable block can be chosen from block copolymers of olefin or of cycloolefin with a crystallizable chain, such as those resulting from the block polymerization of:

cyclobutene, cyclohexene, cyclooctene, norbornene (that is to say, bicyclo[2.2.1]hept-2-ene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene or their mixtures, with ethylene, propylene, 1-butene, 3-methyl-1-butene, 1-hexene, 4-methyl-1-pentene, 1-octene, 1-decene, 1-eicosene or their mixtures, and in particular copoly(ethylene/norbornene) blocks and (ethylene/propylene/ethylidenenorbornene) terpolymer blocks. Use may also be made of those resulting from the block copolymerization of at least 2 $C_2$-$C_{16}$ α-olefins and better still $C_2$-$C_{12}$ α-olefins, such as those mentioned above, and in particular the block bipolymers of ethylene and 1-octene.

The polymer carrying, in the backbone, at least one crystallizable block can be chosen from copolymers exhibiting at least one crystallizable block, the remainder of the copolymer being amorphous (at ambient temperature). These copolymers can, in addition, exhibit two crystallizable blocks of different chemical natures.

The preferred copolymers are those which have, at ambient temperature, both a crystallizable block and a both hydrophobic and lipophilic amorphous block which are sequentially distributed. Mention may be made, for example, of the polymers having one of the following crystallizable blocks and one of the following amorphous blocks:

block crystallizable by nature of polyester type, such as poly(alkylene terephthalate)s, or of polyolefin type, such as polyethylenes or polypropylenes; and amorphous and lipophilic block, such as amorphous polyolefins or copoly(olefin)s, for example poly(isobutylene), hydrogenated polybutadiene or hydrogenated poly(isoprene).

Mention may be made, as examples of such copolymers with a crystallizable block and with an amorphous block, of:

α) poly(ε-caprolactone)-b-poly(butadiene) block copolymers, preferably used hydrogenated, such as those described in the paper, "Melting behavior of poly(ε-caprolactone)-block-polybutadiene copolymers", by S. Nojima, Macromolecules, 32, 3727-3734 (1999), β) block or multiblock hydrogenated poly(butylene terephthalate)-b-poly(isoprene) block copolymers, cited in the paper, "Study of morphological and mechanical properties of PP/PBT", by B. Boutevin et al., Polymer Bulletin, 34, 117-123 (1995), γ) the poly(ethylene)-b-copoly(ethylene/propylene) block copolymers cited in the papers, "Morphology of semi-crystalline block copolymers of ethylene-(ethylene-alt-propylene)", by P. Rangarajan et al., Macromolecules, 26, 4640-4645 (1993) and, "Polymer aggregates with crystalline cores: the system poly(ethylene)-poly(ethylene-propylene)", P. Richter et al., Macromolecules, 30, 1053-1068 (1997), and δ) the poly(ethylene)-b-poly(ethylethylene) block copolymers cited in the general article, "Crystallization in block copolymers", by I. W. Hamley, Advances in Polymer Science, vol. 148, 113-137 (1999).

C) Polycondensates of Aliphatic or Aromatic or Aliphatic/Aromatic Polyester Type According to a third embodiment, the semi-crystalline polymer is chosen from polycondensates of aliphatic or aromatic or aliphatic/aromatic polyester type.

The polyester polycondensates can be chosen from aliphatic polyesters. Their molecular mass is preferably greater than or equal to 200 and less than or equal to 10 000 and more preferably greater than or equal to 300 and less than or equal to 5000, preferably greater than or equal to 500 and less than or equal to 2000 g/mol.

The polyester polycondensates are chosen in particular from polycaprolactones. In particular, the polycaprolactones can be chosen from ε-caprolactone homopolymers. Homopolymerization can be initiated with a diol, in particular a diol having from 2 to 10 atoms, such as diethylene glycol, 1,4-butanediol or neopentyl glycol.

Use may be made, for example, of polycaprolactones, in particular those sold under the names Capa® 240 (melting point of 68° C. and molecular weight of 4000), 223 (melting point of 48° C. and molecular weight of 2000), 222 (melting point of 48° C. and molecular weight of 2000), 217 (melting point of 44° C. and molecular weight of 1250), 2125 (melting point of 45° C. and molecular weight of 1250), 212 (melting point of 45° C. and molecular weight of 1000), 210 (melting point of 38° C. and molecular weight of 1000) and 205 (melting point of 39° C. and molecular weight of 830) by Solvay and PCL-300 and PCL-700 by Union Carbide.

Use may in particular be made of Capa® 2125, the melting point of which is between 35 and 45° C. and the weight-average molecular mass of which is equal to 1250.

The semi-crystalline polymers of the composition of the invention may or may not be partially crosslinked provided that the degree of crosslinking is not harmful to their dissolution or dispersion in the fatty phase by heating above their melting point. The crosslinking can then be chemical crosslinking, by reaction with a multifunctional monomer during the polymerization. It can also be physical crosslinking, which can then be due either to the establishment of bonds of hydrogen or dipolar type between groups carried by the polymer, such as, for example, dipolar interactions between carboxylate ionomers, these interactions being low in degree and carried by the backbone of the polymer, or to phase separation between the crystallizable blocks and the amorphous blocks carried by the polymer.

The semi-crystalline polymers of the composition according to the invention are preferably not crosslinked.

In practice, the total amount of semi-crystalline polymer(s) represents from 0.1 to 20% by weight, relative to the total weight of the composition, better still from 0.1 to 10% and even better still from 0.1 to 5%.

Fillers

A makeup and/or care composition according to the invention may also comprise one or more filler(s).

According to a first embodiment, the composition is free of fillers.

According to a second preferred embodiment, the composition comprises at least one or more filler(s).

The term "fillers" should be understood as meaning colorless or white, mineral or synthetic particles of any shape, which are insoluble in the medium of the composition, irrespective of the temperature at which the composition is manufactured. These fillers serve especially to modify the rheology or the texture of the composition.

The fillers may be mineral or organic and of any shape, platelet-shaped, spherical or oblong, irrespective of the crystallographic form (for example lamellar, cubic, hexagonal, orthorhombic, etc.). Mention may be made of talc, mica, silica, kaolin, clay, bentone, fumed silica particles, optionally hydrophilic- or hydrophobic-treated, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning) and silicone resin microbeads (for example Tospearls® from Toshiba), precipitated calcium carbonate, magnesium carbonate, magnesium hydrogen carbonate, hydroxyapatite, hollow silica microspheres (Silica Beads® from Maprecos), elastomeric polyorganosiloxane particles, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, and mixtures thereof.

They may also be particles comprising a copolymer, said copolymer comprising trimethylol hexyl lactone. In particular, it may be a copolymer of hexamethylene diisocyanate/trimethylol hexyl lactone. Such particles are especially commercially available, for example, under the name Plastic Powder D-400® or Plastic Powder D-800® from the company Toshiki.

According to a preferred embodiment, the composition according to the invention comprises at least silica, preferably hydrophobic treated silica.

According to one preferred embodiment, the composition comprises at least one filler, and in particular chosen from fumed silicas that have optionally been hydrophilic- or hydrophobic-treated, preferably hydrophobic-treated. Preferably, the composition comprises at least one filler known as Silica Dimethyl Silylate (according to the CTFA).

The hydrophobic groups may especially be dimethylsilyloxyl or polydimethylsiloxane groups, which are especially obtained by treating fumed silica in the presence of polydimethylsiloxane or dimethyldichlorosilane. Silicas thus treated are known as Silica Dimethyl Silylate according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

According to a particular embodiment, the composition according to the invention is free of "nanosilica", preferably free of hydrophobic treated silica of INCI name Silica Dimethyl Silylate. The term "nanosilica" means silica having a nanometric size, or a least a fraction of nanometric size.

Preferably, the composition contains between 0.01% and 25% by weight and in particular between 0.1% and 20% by weight of fillers relative to the total weight of the composition.

Preferably, when the composition is in liquid form, it comprises at least one filler, preferably chosen from silica, kaolin, bentone, fumed silica particles, which have preferably been hydrophobic-treated, lauroyllysine and starch.

Preferably, a composition according to the invention may comprise a filler chosen from:

organomodified clays, which are preferably clays treated with compounds chosen especially from quaternary amines and tertiary amines. Organomodified clays that may be mentioned include organomodified bentonites, such as the product sold under the name Bentone 34 by the company Rheox, and organomodified hectorites such as the products sold under the names Bentone 27 and Bentone 38 by the company Rheox, and hydrophobic fumed silica. Such silicas are sold, for example, under the references Aerosil R812® by the company Degussa and Cab-O-Sil TS-530® by the company Cabot, and under the references Aerosil R972® and Aerosil R974® by the company Degussa and Cab-O-Sil TS-610® and Cab-O-Sil TS-720® by the company Cabot.

The filler may be present in a content ranging from 0.1% to 5% by weight and better still from 0.4% to 3% by weight relative to the total weight of the composition.

Hydrophobic Silica Aerogel Particles

According to a preferred embodiment, the composition comprise may comprised at least hydrophobic silica aerogel particles. Such compound is a filler.

Preferably such compound is present when the composition is free of nanosilica and more particularly free of Silica Dimethyl Silylate.

Preferably the hydrophobic silica aerogel particles may be present in a content ranging from 0.1% to 15% by weight and better still from 0.1% to 10% by weight, relative to the total weight of the composition.

Preferably the hydrophobic silica aerogel particles may be present in a content ranging from 0.1% to 6% by weight and better still from 0.2% to 4% by weight, relative to the total weight of the composition.

According to this embodiment, the composition may comprise at least a additional filler, such as those described before for example.

Preferably, the composition according to the invention comprises at least Hydrophobic silica aerogel particles, when the composition is free of nanometric silica particles as described before, such as Silica Dimethyl Silylate.

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles that may be used in the present invention have a specific surface area per unit of mass ($S_M$) ranging from 500 to 1500 $m^2/g$, preferably from 600 to 1200 $m^2/g$ and better still from 600 to 800 $m^2/g$, and a size expressed as the mean volume diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles that may be used in the present invention have a size expressed as the mean volume diameter (D[0.5]) ranging from 1 to 30 μm, preferably from 5 to 25 μm, better still from 5 to 20 μm and even better still from 5 to 15 μm.

The specific surface area per unit of mass may be determined via the BET (Brunauer-Emmett-Teller) nitrogen absorption method described in the Journal of the American Chemical Society, vol. 60, page 309, February 1938 and corresponding to the international standard ISO 5794/1 (appendix D). The BET specific surface area corresponds to the total specific surface area of the particles under consideration.

The size of the hydrophobic silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

According to one advantageous embodiment, the hydrophobic silica aerogel particles used in the present invention have a specific surface area per unit of mass ($S_M$) ranging from 600 to 800 m$^2$/g and a size expressed as the mean volume diameter (D[0.5]) ranging from 5 to 20 μm and better still from 5 to 15 μm.

The hydrophobic silica aerogel particles used in the present invention may advantageously have a tamped density ρ ranging from 0.04 g/cm$^3$ to 0.10 g/cm$^3$ and preferably from 0.05 g/cm$^3$ to 0.08 g/cm$^3$.

In the context of the present invention, this density, known as the tamped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in cm$^3$ and m in g).

According to one embodiment, the hydrophobic silica aerogel particles that may be used in the present invention have a specific surface area per unit of volume $S_v$ ranging from 5 to 60 m$^2$/cm$^3$, preferably from 10 to 50 m$^2$/cm$^3$ and better still from 15 to 40 m$^2$/cm$^3$.

The specific surface area per unit of volume is given by the relationship:

$S_v = S_M \rho$; where ρ is the tamped density expressed in g/cm$^3$ and $S_M$ is the specific surface area per unit of mass expressed in m$^2$/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The oil-absorbing capacity measured at the wet point, noted Wp, corresponds to the amount of water that needs to be added to 100 g of particle in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The hydrophobic silica aerogel particles that may be used according to the present invention are preferably of silylated silica type (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogels particles that have been surface-modified by silylation, reference may be made to document U.S. Pat. No. 7,470,725.

Use will be made in particular of hydrophobic silica aerogels particles surface-modified with trimethylsilyl groups.

As hydrophobic silica aerogel particles that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by the company Cabot under the references Aerogel TLD 201, Aerogel OGD 201, Aerogel TLD 203, and ENOVA AEROGEL MT 1100.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m$^2$/g (oil uptake equal to 1080 ml/100 g).

Advantageously, the hollow particles in accordance with the invention are at least partly formed from hydrophobic silica aerogel particles, preferably those with a specific surface area per unit of mass ($S_M$) ranging from 500 to 1500 m$^2$/g and preferably from 600 to 1200 m$^2$/g, and a size expressed as the mean volume diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

The use of hydrophobic silica aerogel particles, also advantageously makes it possible to improve the stability of the composition.

Dextrin Ester

The composition according to the invention may comprise at least an ester of dextrin, preferably an ester of dextrin and a fatty acid, preferably a $C_{12}$-$C_{24}$ fatty acid.

Preferably, the dextrin ester is an ester of dextrine and a $C_{14}$-$C_{18}$ fatty acid.

Preferably, the dextrin ester is dextrine palmitate, for example such as those commercialised under the references Rheopearl TL® or Rheopearl KL® by the society CHIBA FLOUR.

A composition according to the invention may comprise a content of dextrin ester ranging from from 0.1% to 15% by weight and preferably from 0.5% to 10% by weight, relative to the total weight of the composition.

A composition according to the invention may comprise a content of dextrin ester ranging from 1% to 8% by weight and preferably from 2% to 6% by weight, relative to the total weight of the composition.

According to a preferred embodiment, the composition according to the invention, the composition is free from dextrin ester.

Dyestuffs

The compositions according to the invention may preferably comprise at least one dyestuff (also known as a colouring agent), which may be chosen from water-soluble or liposoluble dyes, pigments and nacres, and mixtures thereof.

The composition according to the invention may also comprise one or more dyestuffs chosen from water-soluble dyes and pulverulent dyestuffs, for instance pigments, nacres and glitter flakes that are well known to those skilled in the art.

The dyestuffs may be present in the composition in a content ranging from 0.01% to 30% by weight, relative to the weight of the composition, preferably from 0.1% to 20% by weight.

The term "pigments" should be understood as meaning white or coloured, mineral or organic particles that are insoluble in an aqueous solution, which are intended to colour and/or opacify the resulting film.

The pigments may be present in a proportion of from 0.01% to 30% by weight, especially from 0.1% to 25% by weight and in particular from 0.2% to 15% by weight relative to the total weight of the cosmetic composition.

As mineral pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The dyestuff may also comprise a pigment with a structure that may be, for example, of silica microsphere type containing iron oxide. An example of a pigment having this structure is the product sold by the company Miyoshi under the reference PC Ball PC-LL-100 P, this pigment consisting of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP-A-542 669, EP-A-787 730, EP-A-787 731 and WO-A-96/08537.

The term "nacres" should be understood as meaning coloured particles of any form, which may or may not be iridescent, especially produced by certain molluscs in their shell, or alternatively synthesized, and which have a colour effect via optical interference.

The nacres may be chosen from nacreous pigments such as titanium mica coated with an iron oxide, mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

As illustrations of nacres that may be used in the context of the present invention, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

The term "dyes" should be understood as meaning compounds that are generally organic, which are soluble in fatty substances such as oils or in an aqueous-alcoholic phase.

The cosmetic composition according to the invention may also comprise water-soluble or liposoluble dyes. The liposoluble dyes are, for example, Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

The cosmetic composition according to the invention may also contain at least one material with a specific optical effect as dyestuff.

This effect is different from a simple conventional hue effect, i.e. a unified and stabilized effect as produced by standard dyestuffs, for instance monochromatic pigments. For the purposes of the invention, the term "stabilized" means lacking an effect of variability of the colour as a function of the angle of observation or alternatively in response to a temperature change.

For example, this material may be chosen from particles with a metallic tint, goniochromatic coloring agents, diffracting pigments, thermochromic agents, optical brighteners, and also fibres, especially interference fibres. Needless to say, these various materials may be combined so as to afford the simultaneous manifestation of two effects, or even of a novel effect in accordance with the invention.

Aqueous Phase

A composition according to the invention may also comprise an aqueous phase, which may represent 0.01% to 50% by weight, especially 0.1% to 30% by weight or even 1% to 20% by weight relative to the total weight of the composition. This aqueous phase may be formed essentially from water, or may comprise a mixture of water and of water-miscible solvent (miscibility in water of greater than 50% by weight at 25° C.) chosen especially from monoalcohols containing 1 to 5 carbon atoms such as ethanol, isopropanol, glycols containing 2 to 8 carbon atoms such as propylene glycol, ethylene glycol, 1,3-butylene glycol, dipropylene glycol, $C_3$-$C_4$ ketones and $C_2$-$C_4$ aldehydes, and mixtures thereof.

However, as stated above, advantageously, the compositions according to the invention are anhydrous.

The term "anhydrous" especially means that water is preferably not deliberately added to the compositions, but may be present in trace amounts in the various compounds used in the compositions.

Additive(s)

A makeup and/or care composition according to the invention may also comprise at least one agent usually used in cosmetics, chosen, for example, from reducing agents, thickeners, film-forming agents that are especially hydrophobic, silicone elastomers, softeners, antifoams, moisturizers, UV-screening agents, ceramides; cosmetic active agents; peptizers, fragrances, proteins, vitamins, propellants, hydrophilic or lipophilic, film-forming or non-film-forming polymers; lipophilic or hydrophilic gelling agents. The above additives are generally present in an amount for each of them of between 0.01% and 10% by weight relative to the total weight of the composition. Needless to say, a person skilled in the art will take care to select the constituents of the composition such that the advantageous properties associated with the invention are not, or are not substantially, adversely affected.

Usual Additional Cosmetic Ingredients

A composition used according to the invention may also comprise any usual cosmetic ingredient, which may be chosen especially from antioxidants, film-forming polymers, fragrances, preserving agents, emollients, moisturizers, neutralizers, sunscreens, sweeteners, vitamins, free-radical scavengers and sequestrants, and mixtures thereof.

The amounts of each of these various ingredients are those conventionally used in the fields under consideration, and range, for example, from 0.01% to 10% by weight relative to the total weight of the composition.

Needless to say, a person skilled in the art will take care to select the optional additional ingredients and/or the amount thereof such that the advantageous properties of the composition according to the invention are not, or are not substantially, adversely affected by the envisaged addition.

A composition in accordance with the invention may be in liquid form or in solid form.

According to a first embodiment, the composition is in solid form. In particular, it may be a cosmetic product chosen from a lip balm and/or a lipstick. This product may preferably be in the form of a stick or cast in a dish.

According to one embodiment, it is a lipstick or a lip balm in stick form.

A composition according to the invention may constitute a liquid lipstick for the lips, a body makeup product, a facial or body care product or an antisun product.

According to one preferred embodiment, a composition of the invention is in liquid form. As illustrations of liquid formulations, mention may be made especially of lip glosses.

As stated previously, the composition according to the invention is homogeneous and stable and gives access to a deposit on the skin or the lips that has good cosmetic properties, in particular in terms of gloss, comfort (thickness deposit) and absence of transfer of the deposit. In particular, compositions according to the invention enable forming a deposit exhibits no color transfer, in particular on a cup while drinking for a lip product, and when the composition contains one or more colouring agent(s).

EXAMPLES

In the description and in the examples that follow, unless otherwise mentioned, the percentages are weight percentages and the ranges of values given in the form "between . . . and . . . " include the stated lower and upper limits.

Unless otherwise mentioned, the values in the example below are expressed as % by weight relative to the total weight of the composition.

The examples below are presented as non-limiting illustrations of the field of the invention.

Examples 1 to 3 of Cosmetic Formulae of Liquid Lip Product Type (Gloss)

Three liquid makeup formulae having the following compositions were prepared (the percentages indicated are weight percentages). Formula 1 illustrates the invention, and formula 2 and 3 are comparative compositions outside the invention.

| INCI US NAME and Commercial references | Formula 1 according to the invention (% in weight) | Comparative Formula 2 not belonging to the invention (% in weight) | Comparative Formula 3 not belonging to the invention (% in weight) |
|---|---|---|---|
| HYDROGENATED POLYISOBUTENE (Parleam Lite from Nof Corporation) | 20.34 | 21.89 | 21.89 |
| OCTYLDODECYL NEOPENTANOATE | 22.46 | 24 | 24 |
| Isopropyl Isostearate | 2.63 | 2.3 | 2.3 |
| Hydrogenated castor oil isostearate (Salacos HCIS V-L from Nisshin Oillio) | 6.79 | 7 | 7 |

-continued

| INCI US NAME and Commercial references | Formula 1 according to the invention (% in weight) | Comparative Formula 2 not belonging to the invention (% in weight) | Comparative Formula 3 not belonging to the invention (% in weight) |
|---|---|---|---|
| Bis-diglyceryl polyacyladipate-2 (Softisan 649 from Sasol) | 6.79 | 7 | 7 |
| Hydrogenated styrene/butadiene copolymer (Kraton G1657M from Kraton Polymers) | 7.38 | 7 | 7 |
| Hydrogenated styrene/methylstyrene/indene copolymer (Regalite R1100 from Eastman Chemical) | 15.8 | 15 | 15 |
| Red 7 | 0.24 | 0.24 | 0.24 |
| Iron Oxide | 0.07 | 0.07 | 0.07 |
| MICA (and) IRON OXIDES | 1.50 | 1.50 | 1.50 |
| Silica Dimethyl Silylate (Aerosil R972 from Evonik Degussa) | 4 | 4 | 4 |
| Dimethicone (XIAMETER PMX-200 SILICONE FLUID 350CS from Dow Corning) | 6 | 5.00 | — |
| Dimethicone (XIAMETER PMX-200 SILICONE FLUID 100CS from Dow Corning) | 6 | 5.00 | — |
| Hydrogenated polydecene (Puresyn 6 from ExxonMobil Chemical) | — | — | 10 |
| TOTAL | 100 | 100 | 100 |

Preparation Process

The compositions of Examples 1 to 3 were obtained according to the following protocol:

In a first stage, the fillers, pigments and/or active agents of the fatty phase were ground in a three-roll mill in part of the oily phase (Polar Oil is preferred like OCTYLDODECYL NEOPENTANOATE.

In parallel, a pregel was prepared for dispersion of the hydrocarbon-based resin and the hydrocarbon-based block copolymer in part of the oil selected from low viscosity Oils less than 1 PaS. (HYDROGENATED POLYISOBUTENE (Parleam Lite from NOF) and OCTYLDODECYL NEOPENTANOATE, Polydecene (Puresyn 6 from ExxonMobil Chemical)). This pregel was introduced into a heating pan. The rest of the liposoluble ingredients were then mixed in the heating pan at a temperature of about 100° C. with Rayneri blending until a homogeneous mixture was obtained. The ground pigmentary material was then incorporated into the mixture, along with the nacres, if present, and stirring was continued until the mixture was homogeneous.

The mixture has then been cooled down while slowly mixing, and was dropped in bulk at 40° C. The composition is then left at room temperature for 24 hours.

Evaluation

The viscosity of compositions 1 to 3 at 25° C. was evaluated according to the protocol described previously.

Each of the compositions obtained was placed for 72 hours at 24° C. and at 42° C. in order to evaluate the stability of the composition. More particularly, it is observed if the compositions remain homogenous (no phase separation and/or no sedimentation of the pigments)

Each of the compositions was then applied to the lips in order to evaluate the application properties and the characteristics of the deposit obtained (Shine, Color Transfer resistance, and tack).

The tacky nature of a deposit made on the lips with the formula to be evaluated was evaluated 5 minutes after application by applying a finger onto the deposit made from the formula to be evaluated and the tack was assessed by the person on removal of her upper and lower lips.

The color transfer resistance is evaluated by applying the lips on a white cup as while drinking 5 minutes after applying the compositions on the lips.

| PROPERTIES | Formula 1 according to the invention | Comparative Formula 2 not belonging to the invention | Comparative Formula 3 not belonging to the invention |
|---|---|---|---|
| Viscosity | Comprised between 7 and 11.5 Pa · s | Comprised between 7 and 11.5 Pa · s | Comprised between 7 and 11.5 Pa · s |
| Stability after 72 hours at 24° C. | Yes | Yes | Yes |
| Stability after 72 hours at 47° C. | Yes | Yes | Yes |
| Application properties (glide and easiness to apply) | Good | Good | Too thin film |
| Shine of the deposit | Good | Good | Not Good |
| Tackiness of the deposit while drying | Good = sparingly tacky | Good | Tacky |
| Color Transfer resistance | Good | Not Good | Not Good |

The comparative Formula 2 out of the invention, having 10% of non phenylated dimethicone oil, has good application properties (smooth and homogeneous deposit) and the deposit obtained on the lips with this formula has not a good color transfer resistance. The deposit on the lips obtained with formula 2 has a good level of shine, and is sparingly tacky.

The comparative Formula 3 out of the invention, having no non volatile silicon oil (have been replaced with 10% hydrogenated polydecene), does not have good application properties, because the the film obtained is too thin (not thick enough) and the deposit obtained on the lips with this formula has a bad color transfer resistance. The deposit made with formula 3 has a middle shine level and is quite tacky.

On the contrary, Formula 1 according to the invention that has 12% non volatile dimethicone oil has good application properties (smooth and the deposit is homogenous and thick enough) and has a good color transfer resistance (almost no colour on the cup). The deposit made with Formula 1 is sparingly tacky and has a good level of shine.

Examples 4 to 6 of Cosmetic Formulae of Liquid Lip Product Type (Gloss)

Three liquid makeup formulae having the following compositions were prepared (the percentages indicated are weight percentages). Formulae 4 to 6 illustrate the invention.

| INCI US NAME And Commercial references | Formula 4 according to the invention (% in weight) | Formula 5 according to the invention (% in weight) | Formula 6 according to the invention (% in weight) |
| --- | --- | --- | --- |
| HYDROGENATED POLYISOBUTENE (Parleam Lite from Nof Corporation) | 19.61 | 18.37 | 17.12 |
| OCTYLDODECYL NEOPENTANOATE | 21.64 | 20.27 | 18.91 |
| Isopropyl Isostearate | 2.53 | 2.37 | 2.21 |
| Hydrogenated castor oil isostearate (Salacos HCIS V-L from Nisshin Oillio) | 6.54 | 6.13 | 5.72 |
| Bis-diglyceryl polyacyladipate-2 (Softisan 649 from Sasol) | 6.54 | 6.13 | 5.72 |
| Hydrogenated styrene/butadiene copolymer (Kraton G1657M from Kraton Polymers) | 7.11 | 6.66 | 6.21 |
| Hydrogenated styrene/methylstyrene/indene copolymer (Regalite R1100 from Eastman Chemical) | 15.22 | 14.26 | 13.3 |
| Red 7 (Unipure Red LC 3079 OR from Sensient) | 0.24 | 0.24 | 0.24 |
| Iron Oxide (Sunpuro Black Iron Oxide from SUN) | 0.07 | 0.07 | 0.07 |
| MICA (and) IRON OXIDES (Colorona Glitter Bordeaux from Merck) | 1.50 | 1.50 | 1.50 |
| SILICA DIMETHYL SILYLATE (Aerosil R972 from Evonik Degussa) | 4 | 4 | 4 |
| Dimethicone (XIAMETER PMX-200 SILICONE FLUID 350CS from Dow Corning) | 7.5 | 10 | 12.5 |
| Dimethicone (XIAMETER PMX-200 SILICONE FLUID 100CS from Dow Corning) | 7.5 | 10 | 12.5 |
| TOTAL | 100 | 100 | 100 |

Compositions 4 to 6 are prepared and evaluated in the same manner as described before.

The results are the following.

| PROPERTIES | Formula 4 according to the invention | Formula 5 according to the invention | Formula 6 according to the invention |
| --- | --- | --- | --- |
| Viscosity | Comprised between 7 and 11.5 Pa · s | Comprised between 7 and 11.5 Pa · s | Comprised between 7 and 11.5 Pa · s |
| Stability after 72 hours at 24° C. | Yes | Yes | Yes |
| Stability after 72 hours at 47° C. | Yes | Yes | Yes |
| Application properties (glide and easiness to apply) | Very Good | Good | Good |
| Shine of the deposit | Very Good | Very Good | Very Good |
| Tackiness of the deposit while drying | Good = sparingly tacky | Good = sparingly tacky | Very Good = non tacky |
| Color Transfer resistance | Good | Good | Good |

All of the Formula 4 to 6 according to the invention have the same total content of non volatile phenyl dimethicone oil (25%), and have good application properties (smooth and glide). All of the deposits obtained on the lips with these formulae exhibit good color transfer resistance (almost no colour on the cup). Beside, the deposits made with Formula 4 to 6 are sparingly tacky or non tacky.

All of the deposits made with formulas 4 to 6 have a very good shine level (very shiny).

Comparative Examples 7 to 9: Formulae of Liquid Lip Product Type (Gloss)

Six liquid makeup formulae having the following compositions were prepared (the percentages indicated are weight percentages). Formulae 7a, 7b, 8a, 8b, 9a and 9b are comparative formulas not belonging to the invention.

| INCI US NAME and commercial references | Comparative formula 7a not belonging to the invention (% by weight) | Comparative formula 7b not belonging to the invention (% by weight) | Comparative formula 8a not belonging to the invention (% by weight) | Comparative formula 8b not belonging to the invention (% by weight) | Comparative formula 9a not belonging to the invention (% by weight) | Comparative formula 9b not belonging to the invention (% by weight) |
|---|---|---|---|---|---|---|
| HYDROGENATED POLYISOBUTENE (Parleam Lite from Nof Corporation) | 21.89 | 21.89 | 20.34 | 20.34 | 19.61 | 19.61 |
| OCTYLDODECYL NEOPENTANOATE | 24 | 24 | 22.46 | 22.46 | 21.64 | 21.64 |
| Isopropyl Isostearate | 2.3 | 2.3 | 2.63 | 2.63 | 2.53 | 2.53 |
| Hydrogenated castor oil isostearate (Salacos HCIS V-L from Nisshin Oillio) | 7 | 7 | 6.79 | 6.79 | 6.54 | 6.54 |
| Bis-diglyceryl polyacyladipate-2 (Softisan 649 from Sasol) | 7 | 7 | 6.79 | 6.79 | 6.54 | 6.54 |
| Hydrogenated styrene/butadiene copolymer (Kraton G1657M from Kraton Polymers) | 7 | 7 | 7.38 | 7.38 | 7.11 | 7.11 |
| Hydrogenated styrene/methylstyrene/indene copolymer (Regalite R1100 from Eastman Chemical) | 15 | 15 | 15.8 | 15.8 | 15.22 | 15.22 |
| Red 7 | 0.24 | 0.24 | 0.24 | 0.24 | 0.24 | 0.24 |
| Iron Oxide | 0.07 | 0.07 | 0.07 | 0.07 | 0.07 | 0.07 |
| MICA (and) IRON OXIDES | 1.50 | 1.50 | 1.50 | 1.50 | 1.50 | 1.50 |
| SILICA DIMETHYL SILYLATE (Aerosil R972 from Evonik Degussa) | 4 | 4 | 4 | 4 | 4 | 4 |
| TRIMETHYLSILOXYPHENYL DIMETHICONE (Belsil PDM 1000 from Wacker) | 10 | | 12 | | 15 | |
| TRIMETHYL PENTAPHENYL TRISILOXANE (Dow Corning PH-1555 HRI Cosmetic fluid by Dow Corning) | | 10 | | 12 | | 15 |
| TOTAL | 100 | 100 | 100 | 100 | 100 | 100 |

Compositions 7a, 7b, 8a, 8b, 9a and 9b are prepared in the same manner as described before.

Compositions 7a and 7b are similar to comparative composition 2, wherein the non volatile non phenylated dimethicone has been replaced weight by weight by non volatile phenylated silicone oil (10%).

Compositions 8a and 8b are similar to composition 1, wherein the non volatile non phenylated dimethicone has been replaced weight by weight by non volatile phenylated silicone oil (12%).

Compositions 9a and 9b are similar to composition 4, wherein the non volatile non phenylated dimethicone has been replaced weight by weight by non volatile phenylated silicone oil (5%).

All of the compositions 7a, 7b, 8a, 8b, 9a and 9b are homogeneous and stable.

The color non transfer resistance of each of the formulas has been evaluated as described before. The results are the following:

| | Comparative formula 7a not belonging to the invention | Comparative formula 7b not belonging to the invention | Comparative formula 8a not belonging to the invention | Comparative formula 8b not belonging to the invention | Comparative formula 9a not belonging to the invention | Comparative formula 9b not belonging to the invention |
|---|---|---|---|---|---|---|
| Color Transfer resistance | Bad | Bad | Bad | Bad | Bad | Bad |

None of the deposits realised with the comparative formulas 7a, 7b, 8a, 8b, 9a and 9b has a good color transfer resistance. On contrary, composition 1 and 4 belonging to the invention and comprising at least 12% non volatile non phenylated dimethicone oils have a good color transfer resistance.

Examples 10 and 11 of Cosmetic Formulae of Liquid Lip Product Type (Gloss)

The liquid makeup formulas having the following composition was prepared (the percentages indicated are weight percentages). Formula 10 and 11 illustrate the invention.

| INCI US NAME and Commercial references | Formula 10 according to the invention (% in weight) | Formula 11 according to the invention (% in weight) |
|---|---|---|
| HYDROGENATED POLYISOBUTENE (Parleam Lite from NOF Corporation) | 17.82 | 17.82 |
| OCTYLDODECYL NEOPENTANOATE | 19.67 | 21.12 |
| Isopropyl Isostearate | 1.95 | 1.95 |
| Hydrogenated castor oil isostearate (Salacos HCIS V-L from Nisshin Oillio) | 5.95 | 5.95 |
| Bis-diglyceryl polyacyladipate-2 (Softisan 649 from Sasol) | 5.95 | 5.95 |
| Hydrogenated styrene/butadiene copolymer (Kraton G1657M from Kraton Polymers) | 6.46 | 6.46 |
| Hydrogenated styrene/methylstyrene/indene copolymer (Regalite R1100 from Eastman Chemical) | 13.84 | 13.84 |
| Red 7 | 0.24 | 0.24 |
| Iron Oxide | 0.07 | 0.07 |
| MICA (and) IRON OXIDES | 1.50 | 1.50 |
| SILICA DIMETHYL SILYLATE (Aerosil R972 from Evonik Degussa) | 3 | — |
| SILICA SILYLATE (AEROGEL VM-2270 From DOW CORNING) | — | 2 |
| Dimethicone (XIAMETER PMX-200 SILICONE FLUID 350CS from Dow Corning) | 7.5 | 7.5 |
| Dimethicone (XIAMETER PMX-200 SILICONE FLUID 100CS from Dow Corning) | 7.5 | 7.5 |
| Hydrogenated polydecene (Puresyn 6 from ExxonMobil Chemical) | 8.55 | 8.55 |
| TOTAL | 100 | 100 |

Composition 10 and 11 were prepared and evaluated in the same manner as described before.

The results are the following:

| PROPERTIES | Formula 10 according to the invention | Formula 11 according to the invention |
|---|---|---|
| Viscosity (in Pa · s) | 7.9 | 8.6 |
| Stability after 72 hours at 24° C. | Yes | Yes |
| Stability after 72 hours at 47° C. | Yes | Yes |
| Application properties (glide and easiness to apply) | Very Good | Very Good |
| Shine of the deposit | Very Good | Very Good |
| Tackiness of the deposit while drying | Good = sparingly tacky | Good = sparingly tacky |
| Color Transfer resistance | Good | Good |

Formula 10 according to the invention is homogenous and stable. This formula has good application properties (Smooth and deposit is homogeneous and thick enough), and the deposit obtained on the lips exhibit good color transfer resistance (almost no colour on the cup). Beside, the deposit made with Formula 10 has a good level of shine and is sparingly tacky.

Formula 11 according to the invention is homogenous and stable. This formula has good application properties (Smooth and deposit is homogeneous and thick enough), and the deposit obtained on the lips exhibit good color transfer resistance (almost no colour on the cup). Beside, the deposit made with Formula 11 has a good level of shine and is sparingly tacky.

Example 12 of Cosmetic Formulae of Liquid Lip Product Type (Gloss)

The following composition according to the invention was prepared according to the preceding methods (the percentages indicated are weight percentages).

| INCI US and commercial references | Composition 12 |
|---|---|
| Hydrogenated polydecene (Parleam Lite from NOF Corporation) | 8.55 |
| Isopropyl isostearate | 0.45 |
| Octyldodecyl neopentanoate | 19.67 |
| Polyisobutene | 17.82 |
| Hydrogenated styrene/butadiene copolymer(Kraton G1657M from Kraton Polymers) | 6.46 |
| Hydrogenated styrene/methyl styrene/indene copolymer (Regalite R1100 from Eastman Chemical) | 13.84 |
| Red 7 | 0.24 |
| Iron oxides | 0.07 |
| Mica (and) iron oxides | 1.5 |
| Hydrogenated castor oil isostearate (Salacos HCIS V-L from Nisshin Oillio) | 5.95 |
| Bis-behenyl/isostearyl/phytosteryl dimer dilinoleyl dimer dilinoleate | 5.95 |
| Silica dimethyl silylate (Aerosil R 972 from Evonik industries) | 3 |
| Dimethicone (XIAMETER PMX-200 SILICONE FLUID 350CS from Dow Corning) | 7.5 |
| Dimethicone (XIAMETER PMX-200 SILICONE FLUID 100CS from Dow Corning) | 7.5 |
| Pentylene glycol | 1 |
| Caprylyl glycol | 0.5 |
| | 100 |

Evaluation

The same evaluation methods as detailed in the preceding examples were used.

The properties of the composition are indicated in the table below:

| | |
|---|---|
| Viscosity (Pa · s) | 8.8 |
| Stability after 72 hours at 24° c. | Yes (Good = no separation) |
| Stability after 72 hours at 47° c. | Yes (Good = no separation) |
| Application properties (glide and easiness to apply) | Good |
| Shine of the deposit | Good |
| Tackiness of the deposit while drying | Good = sparingly tacky |
| Color transfer resistance | Very good |
| Tackiness just after application | Good (non Tacky) |

Example 13

The following composition according to the invention was prepared according to the preceding methods (the percentages indicated are weight percentages).

| INCI US and Commercial references | Composition 13 |
|---|---|
| Hydrogenated polydecene (Puresyn 6 from ExxonMobil Chemical) | 8.55 |
| Isopropyl isostearate | 0.45 |
| Octyldodecyl neopentanoate | 19.67 |
| Hydrogenated polyisobutene (Parleam Lite from NOF Corporation) | 17.82 |
| Hydrogenated styrene/butadiene copolymer (Kraton G1657M from Kraton Polymers) | 6.46 |
| Hydrogenated styrene/methyl styrene/indene copolymer (Regalite R1100 from Eastman Chemical) | 13.84 |
| Red 7 | 0.24 |
| Iron oxides | 0.07 |
| Mica (and) iron oxides | 1.5 |
| Hydrogenated castor oil isostearate (Salacos HCIS V-L from Nisshin Oillio) | 5.95 |
| Behenyl/dimer dilinoleyl/glyceryl/phytosteryl dimer dilinoleate (*) | 5.95 |
| Silica dimethyl silylate (Aerosil R 972 from Evonik industries) | 3 |
| Dimethicone (XIAMETER PMX-200 SILICONE FLUID 350CS from Dow Corning) | 7.5 |
| Dimethicone (XIAMETER PMX-200 SILICONE FLUID 100CS from Dow Corning) | 7.5 |
| Pentylene glycol | 1 |
| Caprylyl glycol | 0.5 |
| | 100 |

(*) Synthesis of the behenyl/dimer dilmoleyl/glyceryl/phytosteryl dimer dilinoleate
A hydrogenated dimer acid (Pripol 1006 from Croda Inc.; 1100 g (1.902 mol)), a dimer diol (Pripol 2033, from Croda Inc.; 20.9 g (0.038 mol)), glycerin (74.4 g (0.808 mol)), behenyl alcohol (Stenol 1822A from Cognis; 375.9 g (1.179 mol)) and phytosterol (from ADM, 128.3 g (0.314 mol)) were placed in a reactor equipped with a stirrer, a thermometer and a gas introducing tube.

The mixture was heated to 210° C. to 220° C. under a nitrogen stream to carry out an esterification reaction for 41 hours while water produced during the reaction was distilled off.

Thereby, 1618 g of the target ester was obtained (yield: 99.2%).

The obtained ester was a pale yellow paste. (Gardner color: 1 or less; acid value: 4.0; saponification value: 133.6; hydroxyl value: 6.8)

Evaluation

The same evaluation methods as detailed in the preceding examples were used.

The properties of the composition are indicated in the table below:

| | |
|---|---|
| Viscosity (Pa · s) | 9 |
| Stability after 72 hours at 24° C. | Yes (Good = no separation) |
| Stability after 72 hours at 47° C. | Yes (Good = no separation) |
| Application properties (glide and easiness to apply) | Good |
| Shine of the deposit | Very good |
| Tackiness of the deposit while drying | Good = sparingly tacky |
| Color Transfer resistance | Very good |
| Tackiness just after application | Good (non Tacky) |

The invention claimed is:

1. A cosmetic composition for making up and/or caring for the skin and/or the lips, comprising, in a physiologically acceptable medium, at least one fatty phase comprising:
   at least one hydrocarbon-based resin having a number-average molecular weight of less than or equal to about 10,000 g/mol;
   at least one hydrocarbon-based block copolymer;
   at least one non-volatile, non-phenylated silicone oil having at least one dimethicone part, selected from non-volatile polydimethylsiloxanes (PDMS) having a viscosity of from 100 cSt to 500 cSt, wherein the total amount of non-volatile, non-phenylated silicone oil ranges from 11% to 80% by weight, relative to the total weight of the composition; and
   at least one non-volatile hydrocarbonated apolar oil, wherein the total amount of non-volatile hydrocarbonated apolar oil ranges from about 1% to about 80% by weight, relative to the total weight of the composition.

2. The composition according to claim 1, wherein the at least one hydrocarbon-based resin is an indene hydrocarbon-based resin, which is optionally hydrogenated.

3. The composition according to claim 1, wherein the hydrocarbon-based resin is an indene resin chosen from hydrogenated indene/methylstyrene/styrene copolymers.

4. The composition according to claim 1, wherein the total amount of hydrocarbon-based resin ranges from about 1% to about 45% by weight, relative to the total weight of the composition.

5. The composition according to claim 1, wherein the at least one hydrocarbon-based block copolymer is an amorphous copolymer formed by polymerization of ethylenic carbide monomers containing from 2 to 5 carbon atoms.

6. The composition according to claim 1, wherein the at least one hydrocarbon-based block copolymer is a mixture of styrene-butylene/ethylene-styrene triblock hydrogenated copolymer and of styrene-ethylene/butylene diblock copolymer.

7. The composition according to claim 1, wherein the total amount of hydrocarbon-based block copolymer ranges from about 0.1% to about 20% by weight, relative to the total weight of the composition.

8. The composition according to claim 1, wherein the weight ratio of the total amount of hydrocarbon-based resin to the total amount of hydrocarbon-based block copolymer ranges from about 1 to about 10.

9. The composition according to claim 1, wherein the at least one non-volatile hydrocarbonated apolar oil is chosen from polybutene, hydrogenated polybutene, polyisobutene, hydrogenated polyisobutene, polydecene, hydrogenated polydecene, or mixtures thereof.

10. The composition according to claim 1, wherein the composition further comprises at least one additional non-volatile, non-phenylated silicone oil having at least one dimethicone part.

11. The composition according to claim 10, wherein the weight ratio of the at least one non-volatile, non-phenylated silicone oil having at least one dimethicone part, selected from non-volatile polydimethylsiloxanes (PDMS) having a viscosity of from 100 cSt to 500 cSt; to the at least one additional non-volatile, non-phenylated silicone oil having at least one dimethicone part, ranges from about 0.5 to about 2.

12. The composition according to claim 1, wherein the weight ratio of the total amount of non-volatile apolar hydrocarbonated oil to the total amount of nonvolatile, non-phenylated silicone oil having at least one dimethicone part ranges from about 0.2 to about 10.

13. The composition according to claim 1, wherein the composition further comprises hydrophobic silica aerogel particles.

14. The composition according to claim 13, wherein the hydrophobic silica aerogel particles have at least one of:
   a specific surface area per unit of mass ($S_M$) ranging from about 500 $m^2$/g to about 1500 $m^2$/g,
   a size expressed as the mean volume diameter (D[0.5]), ranging from about 1 μm to about 1500 μm, or
   a tamped density (p) ranging from about 0.04 $g/cm^3$ to about 0.10 $g/cm^3$.

15. The composition according to claim 13, wherein the hydrophobic silica aerogel particles are surface-modified with at least one trimethylsilyl group.

16. The composition according to claim 1, wherein the composition further comprises at least one additional compound, chosen from a hydrocarbonated polar oil, an additional non-volatile silicone oil different from the at least one non-phenylated silicone oil having at least one dimethicone part, a fatty pasty compound, a semi-crystalline polymer, a filler, a coloring agent, or mixtures thereof.

17. The composition according to claim 1, wherein the composition is a lip product, a lipstick, a lipcare product, a lipstick pencil, or a lip gloss.

18. The composition according to claim 1, wherein the composition is liquid.

19. A process for making up and/or caring for the skin and/or the lips, comprising applying to the skin and/or the lips a cosmetic composition comprising, in a physiologically acceptable medium, at least one fatty phase comprising:
- at least one hydrocarbon-based resin having a number-average molecular weight of less than or equal to about 10,000 g/mol;
- at least one hydrocarbon-based block copolymer;
- at least one non-volatile, non-phenylated silicone oil having at least one dimethicone part, selected from non-volatile polydimethylsiloxanes (PDMS) having a viscosity of from 100 cSt to 500 cSt, wherein the total amount of non-volatile, non-phenylated silicone oil ranges from 11% to 80% by weight, relative to the total weight of the composition; and
- at least one non-volatile hydrocarbonated apolar oil, wherein the total amount of non-volatile hydrocarbonated apolar oil ranges from about 1% to about 80% by weight, relative to the total weight of the composition.

* * * * *